(12) United States Patent
Bar et al.

(10) Patent No.: US 10,463,486 B2
(45) Date of Patent: Nov. 5, 2019

(54) PERCUTANEOUS VALVE REPAIR AND REPLACEMENT

(71) Applicant: VALFIX MEDICAL LTD., Tel Aviv (IL)

(72) Inventors: Eli Bar, Megadim (IL); Elad Yaacoby, Kfar Shmuel (IL)

(73) Assignee: VALFIX MEDICAL LTD., Tel Aviv (IL)

(*) Notice: Subject to any disclaimer, the term of this patent is extended or adjusted under 35 U.S.C. 154(b) by 0 days.

(21) Appl. No.: 16/403,554

(22) Filed: May 5, 2019

(65) Prior Publication Data

US 2019/0254824 A1   Aug. 22, 2019

Related U.S. Application Data

(63) Continuation of application No. PCT/IB2018/050555, filed on Jan. 30, 2018.

(60) Provisional application No. 62/453,556, filed on Feb. 2, 2017.

(51) Int. Cl.
*A61F 2/24* (2006.01)

(52) U.S. Cl.
CPC ............ *A61F 2/2427* (2013.01); *A61F 2/243* (2013.01); *A61F 2/2439* (2013.01); *A61F 2/2445* (2013.01); *A61F 2220/0008* (2013.01); *A61F 2220/0016* (2013.01); *A61F 2220/0075* (2013.01); *A61F 2220/0091* (2013.01); *A61F 2230/0023* (2013.01)

(58) Field of Classification Search
CPC ...... A61F 2/2427; A61F 2/243; A61F 2/2439; A61F 2/2445; A61F 2230/0023; A61F 2220/0091; A61F 2220/0016; A61F 2220/0075; A61F 2220/0008

See application file for complete search history.

(56) References Cited

U.S. PATENT DOCUMENTS

| | | | | |
|---|---|---|---|---|
| 6,786,925 B1* | 9/2004 | Schoon | ............... | A61B 17/064 623/2.11 |
| 7,722,666 B2* | 5/2010 | Lafontaine | ............ | A61F 2/2418 623/2.11 |
| 7,988,725 B2 | 2/2011 | Gross et al. | | |
| 8,328,868 B2* | 12/2012 | Paul | .......................... | A61F 2/24 623/2.11 |
| 9,089,313 B2* | 7/2015 | Roue | ................ | A61B 17/00234 |
| 9,132,009 B2 | 9/2015 | Hacohen et al. | | |

(Continued)

OTHER PUBLICATIONS

Bar et al., U.S. Appl. No. 16/358,739, filed Mar. 20, 2019.

*Primary Examiner* — Julian W Woo
(74) *Attorney, Agent, or Firm* — Kligler & Associates

(57) ABSTRACT

An apparatus (20, 20a) includes a plurality of flexible tube guides (35), an annular assembly of tubes (34), each of the tubes being slidably disposed within a respective one of the tube guides, a plurality of threads (58), each of which comprising a distal end that is carried by a respective one of the tubes, and an expandable annular structure (36) coupled to the tube guides, configured to expand the assembly of tubes, from a collapsed configuration, over tissue (42) of a subject, by moving the tube guides radially outward. The apparatus further includes a plurality of control wires (40) coupled to the tube guides, configured to position the tubes, subsequently to the expansion of the assembly, for deployment of the threads from the tubes and into the tissue, by flexing the tube guides.

30 Claims, 14 Drawing Sheets

(56) References Cited

U.S. PATENT DOCUMENTS

| | | | |
|---|---|---|---|
| 9,149,358 B2 * | 10/2015 | Tabor | A61F 2/2412 |
| 9,180,005 B1 | 11/2015 | Lashinski et al. | |
| 9,241,702 B2 | 1/2016 | Maisano et al. | |
| 9,750,607 B2 * | 9/2017 | Ganesan | A61F 2/2403 |
| 9,925,079 B2 * | 3/2018 | Tabor | A61F 2/2412 |
| 10,278,820 B2 | 5/2019 | Bar et al. | |
| 10,335,275 B2 * | 7/2019 | Lashinski | A61B 8/0841 |
| 10,376,361 B2 * | 8/2019 | Gross | A61F 2/2409 |
| 2004/0034380 A1 * | 2/2004 | Woolfson | A61B 17/320016 |
| | | | 606/170 |
| 2006/0135967 A1 | 6/2006 | Realyvasquez | |
| 2007/0016288 A1 * | 1/2007 | Gurskis | A61F 2/2418 |
| | | | 623/2.11 |
| 2008/0306586 A1 | 12/2008 | Cartledge et al. | |
| 2010/0179648 A1 | 7/2010 | Richter et al. | |
| 2012/0059458 A1 | 3/2012 | Buchbinder et al. | |
| 2012/0245604 A1 | 9/2012 | Tegzes | |
| 2012/0283757 A1 | 11/2012 | Miller et al. | |
| 2013/0123910 A1 | 5/2013 | Cartledge et al. | |
| 2013/0304197 A1 | 11/2013 | Buchbinder et al. | |
| 2013/0331930 A1 | 12/2013 | Rowe et al. | |
| 2014/0309730 A1 | 10/2014 | Alon et al. | |
| 2015/0173897 A1 | 6/2015 | Raanani et al. | |
| 2015/0366556 A1 | 12/2015 | Khairkhahan et al. | |
| 2016/0015515 A1 | 1/2016 | Lashinski et al. | |

\* cited by examiner

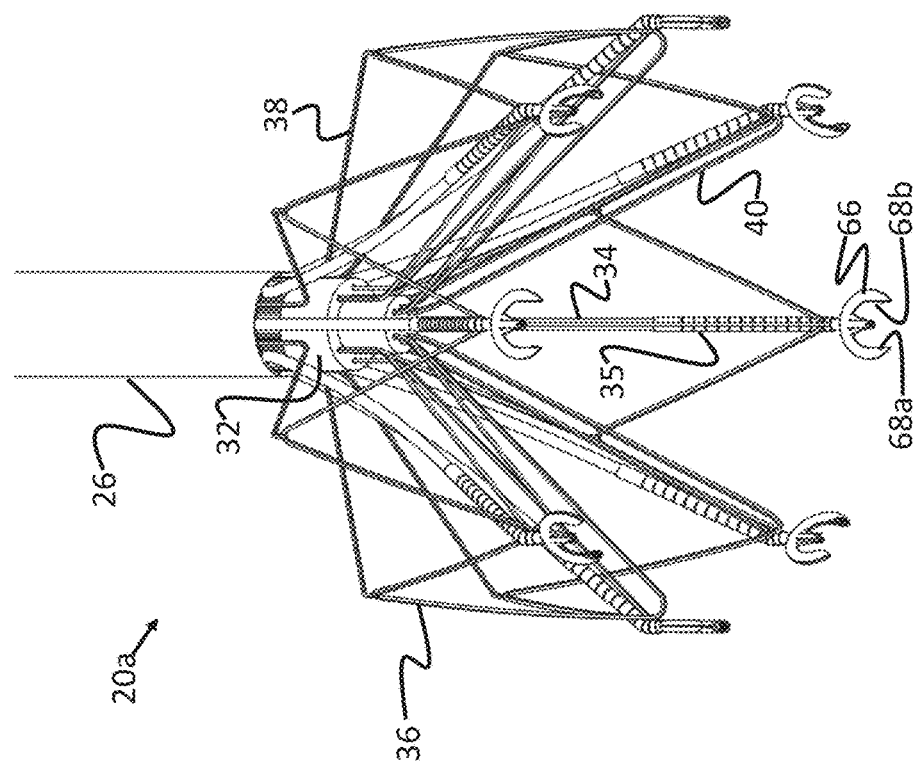
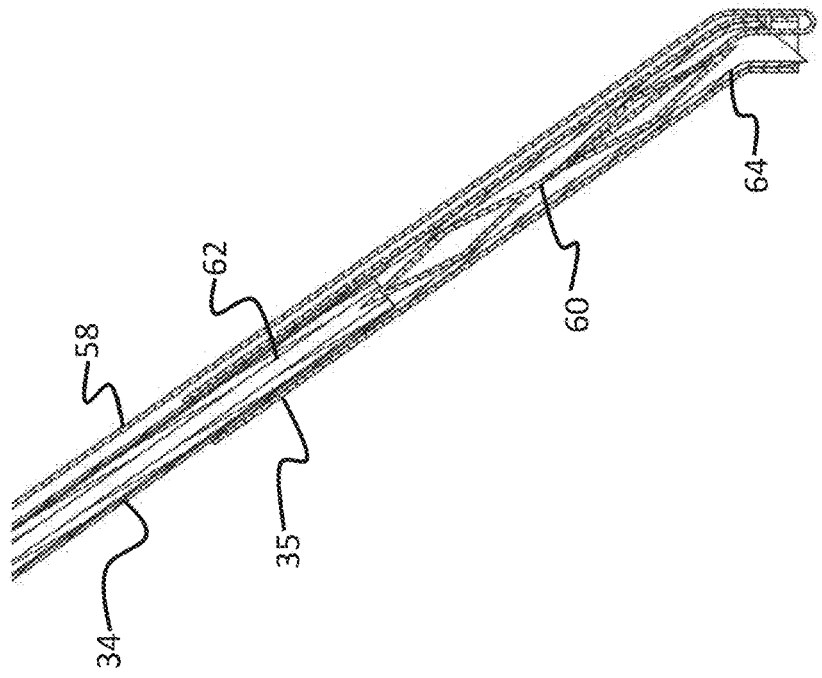

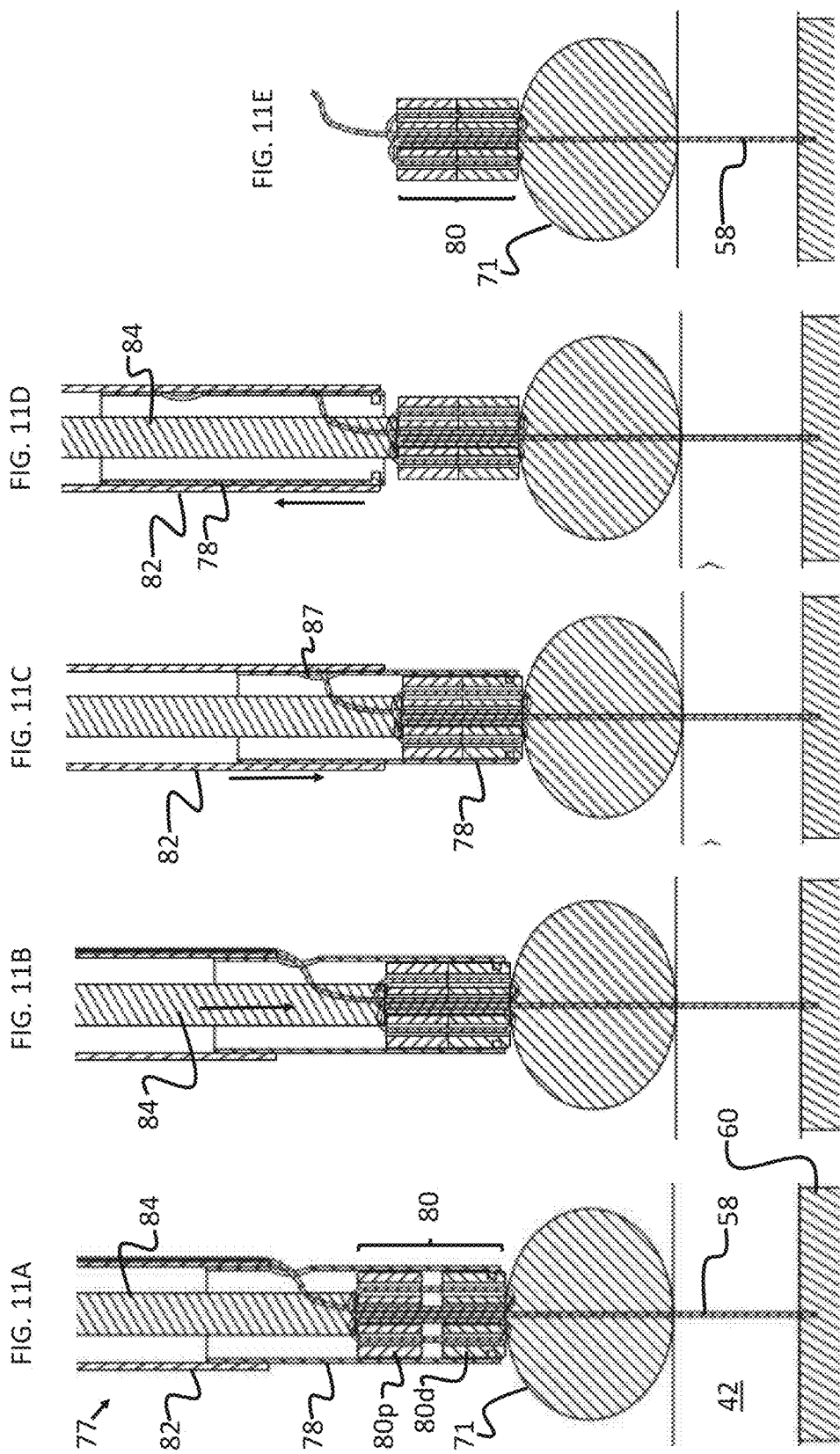

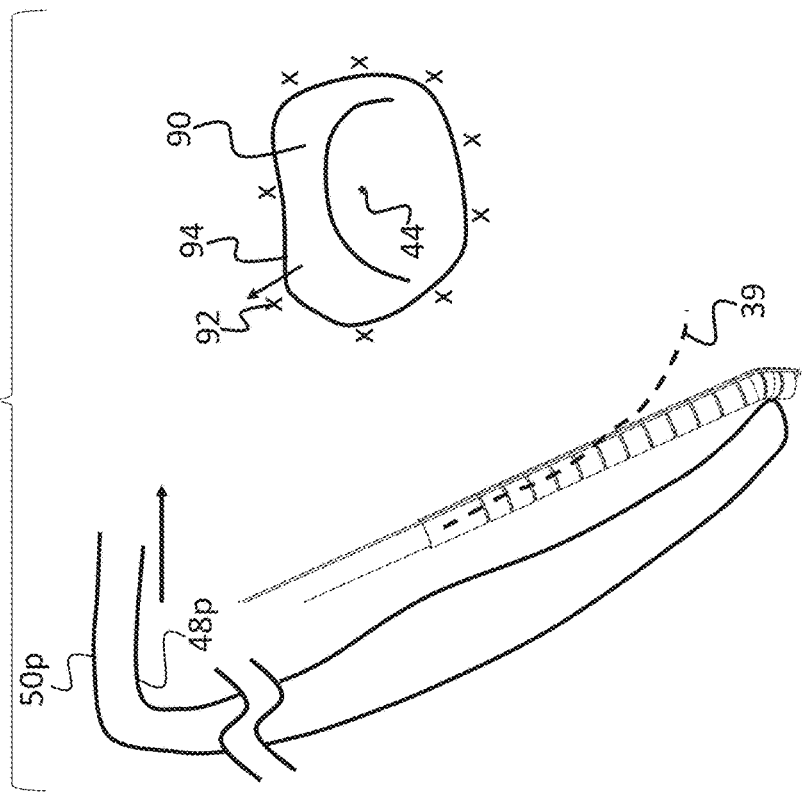
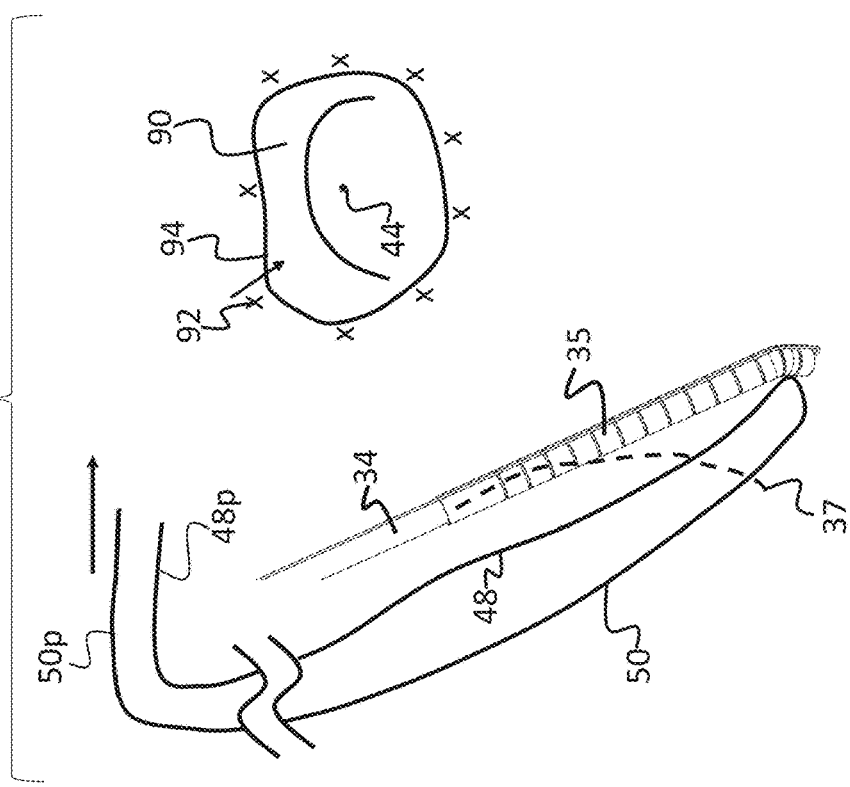

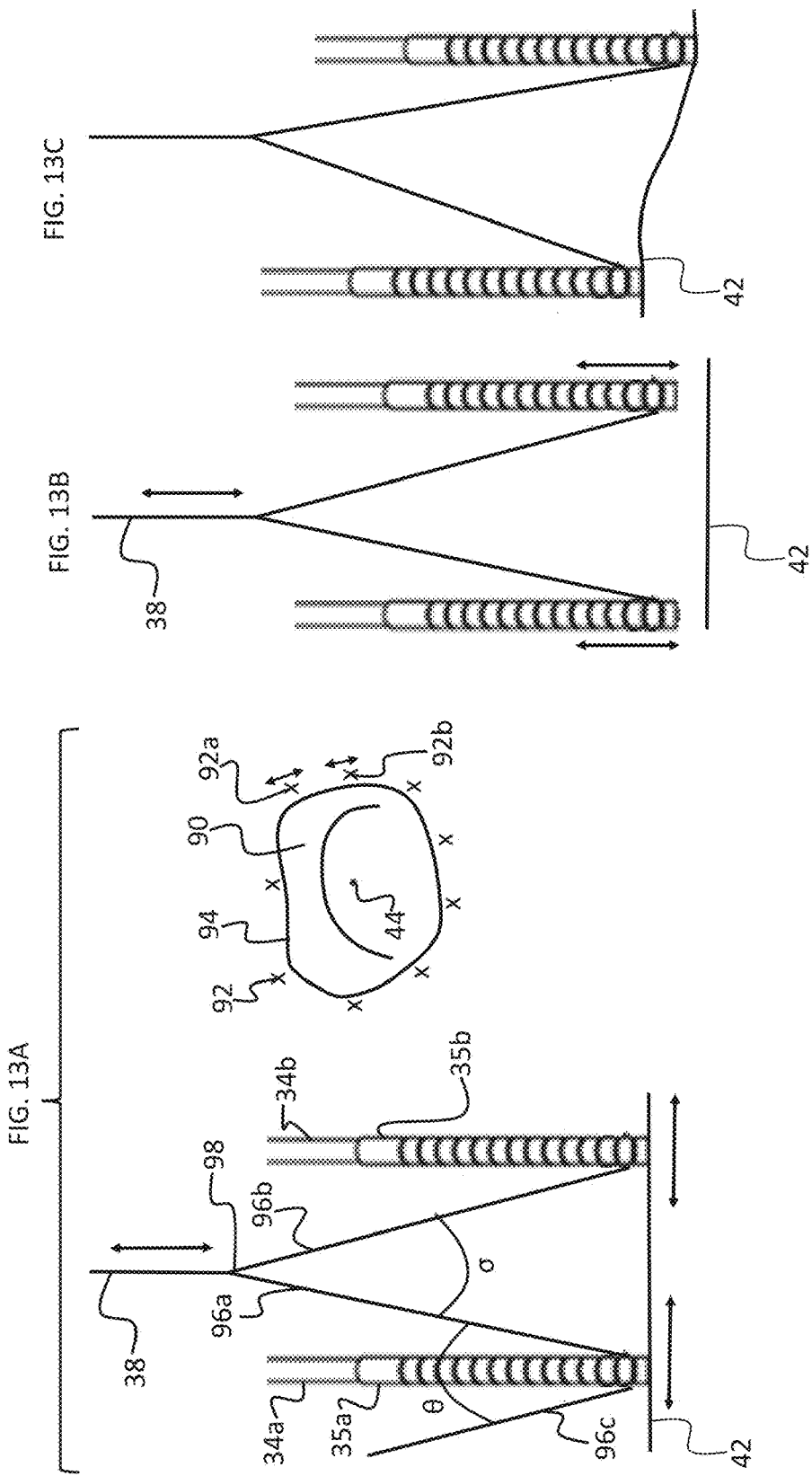

PERCUTANEOUS VALVE REPAIR AND REPLACEMENT

CROSS-REFERENCE TO RELATED APPLICATIONS

The present application is a continuation of, and claims the benefit of, International Patent Application PCT/IB2018/050555, published as WO/2018/142275, filed Jan. 30, 2018, which claims the benefit of U.S. provisional application 62/453,556, entitled "System and method for percutaneous valve repair and replacement," filed Feb. 2, 2017. The respective disclosures of the aforementioned applications are incorporated herein by reference.

FIELD OF THE INVENTION

Embodiments of the present invention relate generally to the field of medical devices, and particularly, to apparatus and methods for percutaneous valve repair and replacement.

BACKGROUND

In some subjects, an implant may be used to repair or replace an intracardiac valve. For example, a replacement valve and/or an annuloplasty ring may be used to repair a regurgitating mitral valve.

International Patent Application Publication WO/2017/187312, whose disclosure is incorporated herein by reference, describes apparatus that includes an assembly of tubes, each one of the tubes being shaped to define a tube lumen. The apparatus further includes a plurality of tissue anchors, each one of the tissue anchors being disposed within a respective one of the tube lumens, an expandable annular structure coupled to the assembly of tubes, and a plurality of control wires coupled to the annular structure, configured to position the tubes for deployment of the tissue anchors from the tube lumens, by manipulating the annular structure.

U.S. Pat. No. 9,132,009 describes apparatus, including one or more valve support guide members configured to be delivered to one or more commissures of a native atrioventricular valve of a patient, one or more valve support anchors configured to be anchored to the one or more commissures of the native valve, a prosthetic valve support advanceable toward the native valve along the one or more valve support guide members and anchored to the native valve at least the one or more commissures, and a prosthetic valve configured to be coupled to the valve support. Other applications are also described.

US Patent Application Publication 2010/0179648 describes a system and process for placing a percutaneous valve device in a body lumen at the location of implantation. Anchors and placement wires or sutures are used to fix the implantation target and guide the device to the implantation site. The system and method are applicable to pre-assembled percutaneous valve devices as well as a modular prosthetic valve device, which modular device is also provided. The modular valve device comprises two or more device modules and is designed to be delivered unassembled and then assembled in the body lumen at or near the site where implantation occurs. The device modules may be assembled before or after the implantation target is fixed with the anchor, and then placed using the placement system in a manner similar to how a pre-assembled percutaneous valve device may be placed in accordance with the invention.

US Patent Application Publication 2012/0283757 describes apparatus for use with an implant configured to be coupled to cardiac tissue of a patient, the apparatus including: a tissue anchor including: a distal tissue coupling element configured to couple the tissue anchor to the cardiac tissue of the patient, and a proximal implant-receiving element configured to receive at least a portion of the implant and facilitate coupling of the implant to the tissue anchor. The proximal implant-receiving element includes an implant-restraining element coupled to a portion of the implant-receiving element, the implant-restraining element being configured to restrain the implant from separating from the implant-receiving element. Other applications are also described.

US Patent Application Publication 2012/0245604 describes a device, kit and method that may include or employ an implantable device (e.g., annuloplasty implant) and a plurality of tissue anchors. The implantable device is positionable in a cavity of a bodily organ (e.g., a heart) and operable to constrict a bodily orifice (e.g., a mitral valve). Each of the tissue anchors may be guided into precise position by an intravascularly or percutaneously techniques. Constriction of the orifice may be accomplished via a variety of structures, for example an articulated annuloplasty ring, the ring attached to the tissue anchors. The annuloplasty ring may be delivered in an unanchored, generally elongated configuration, and implanted in an anchored generally arched, arcuate or annular configuration. Such may approximate the septal and lateral (clinically referred to as anterior and posterior) annulus of the mitral valve, to move the posterior leaflet anteriorly and the anterior leaflet posteriorly, thereby improving leaflet coaptation to reduce mitral regurgitation.

US Patent Application Publication 2006/0135967 describes a valve delivery device and method of use. In one embodiment, the device to deliver a valve prosthesis to a target tissue may include at least one anchor and at least one guide wire coupled to the anchor. The device has a fastener housing. The device may also include a first set of fasteners in said fastener housing, wherein the fasteners are movable from a first position to a second, tissue engagement position. The device may also include a second set of fasteners housed in the anchor to attach the anchor to the tissue, wherein the fasteners are movable from a first position to a second, tissue engagement position. The guide wire may be slidably received in the fastener housing and has a length sufficient to extend from the fastener housing to the target tissue site, wherein the guide wire is used to direct the fastener housing into place.

US Patent Application Publication 2015/0366556 describes a device for use in anchoring an implant, including anchors, sutures, implants, clips, tools, lassos, and methods of anchoring among other methods. Anchors as disclosed therein could be utilized to secure a coaptation assistance device, an annuloplasty ring, an artificial valve, cardiac patch, sensor, pacemaker, or other implants. The implant could be a mitral valve ring or artificial mitral valve in some embodiments.

U.S. Pat. No. 7,988,725 describes an apparatus for repairing a valve of a heart of a patient which includes an annulus and at least first and second leaflets. The apparatus includes an annuloplasty structure, a plurality of tissue anchors, and a plurality of flexible longitudinal guide members removably coupled to the structure. Each of the guide members is configured to facilitate anchoring of the annuloplasty structure to the annulus of the patient by a respective one of the anchors. The guide members are configured to be advanced toward the annulus simultaneously with the annuloplasty structure.

US Patent Application Publication 2014/0309730 describes a heart valve annulus repair device having a tissue engaging member and a plurality of anchors. The tissue engaging member includes a loop of wire. Each of the anchors has a pointy front end and a back end and a slot that runs in a front-to-back direction. The anchors are distributed about the loop of wire with the front ends of the plurality of anchors facing the heart valve annulus and with the loop of wire passing through the slots. The device further includes means for implanting the anchors into the heart valve annulus tissue so that the tissue engaging member becomes affixed to the heart valve annulus.

US Patent Application Publication 2013/0331930 describes systems for implanting annuloplasty rings and other prosthetic devices, which can comprise a plurality of microanchors, sutures threaded through the microanchors, the sutures passing through the prosthetic device, and individual microanchor guides, such as tubes or spears, for each microanchor that contain the microanchors during delivery and allow for positioning and deployment of the microanchors into annular tissue. The systems can also comprise a bracket that is temporarily coupled to the prosthetic device, holds the plurality of microanchor guides in position relative to one another and relative to the prosthetic device, and/or guides the sutures passing through the prosthetic device. The prosthetic device can include suture locking mechanisms to secure the prosthetic device to the sutures and to the implanted microanchors after the deployment devices have been removed.

SUMMARY OF THE INVENTION

There is provided, in accordance with some embodiments of the present invention, apparatus that includes a plurality of flexible tube guides, an annular assembly of tubes, each of the tubes being slidably disposed within a respective one of the tube guides, a plurality of threads, each of which including a distal end that is carried by a respective one of the tubes, and an expandable annular structure coupled to the tube guides. The expandable annular structure is configured to expand the assembly of tubes, from a collapsed configuration, over tissue of a subject, by moving the tube guides radially outward. The apparatus further includes a plurality of control wires coupled to the tube guides, configured to position the tubes, subsequently to the expansion of the assembly, for deployment of the threads from the tubes and into the tissue, by flexing the tube guides.

In some embodiments, the distal end of each one of the threads is disposed over the respective one of the tubes.

In some embodiments, the distal end of each one of the threads is disposed within the respective one of the tubes.

In some embodiments, each one of the tube guides is cylindrical.

In some embodiments, each one of the tube guides is shaped to define a plurality of circumferential grooves, each of the tube guides being flexible by virtue of the grooves.

In some embodiments, each one of the tube guides is coupled to at least one of the control wires.

In some embodiments, each one of the tube guides is coupled to two of the control wires.

In some embodiments, each one of the control wires includes a looped distal end, and each one of the tube guides is coupled to the looped distal end of a respective one of the control wires.

In some embodiments, the looped distal end includes:
an outer arm, to which the tube guide is coupled, disposed at a first radius; and
an inner arm, disposed at a second radius that is smaller than the first radius.

In some embodiments, the tubes include respective pointed distal ends configured to pass through the tissue prior to the deployment of the threads.

In some embodiments, the apparatus further includes:
a plurality of expandable anchors disposed, respectively, within the tubes, and coupled to the respective distal ends of the threads; and
a plurality of anchor-pushing elements disposed, respectively, within the tubes proximally to the anchors, the anchor-pushing elements being configured to deploy the threads by pushing the anchors from the tubes, subsequently to the pointed distal ends of the tubes passing through the tissue.

In some embodiments, the apparatus further includes a slider,
the control wires pass through the slider, and
the slider is configured to expand the assembly of tubes by sliding proximally along the control wires.

In some embodiments, each one of the control wires includes:
a looped distal end;
an outer arm, which extends proximally from the looped distal end, and which passes through the slider at a first radius; and
an inner arm, which extends proximally from the looped distal end, and which passes through the slider at a second radius that is smaller than the first radius.

In some embodiments, the slider includes:
a first cylinder, through which the respective outer arms of the control wires pass; and
a second cylinder, disposed distally from, and being narrower than, the first cylinder, through which the respective inner arms of the control wires pass.

In some embodiments,
the annular structure includes a triangular-wave-shaped ring having alternating top vertices and bottom vertices, and
each one of the bottom vertices is coupled to a respective one of the tube guides.

In some embodiments, respective angles of the top vertices and bottom vertices are adjustable.

In some embodiments, the apparatus further includes a plurality of longitudinal wires coupled to the annular structure, configured to facilitate crimping the annular structure following the deployment of the threads.

In some embodiments, the longitudinal wires are further configured to position the tubes prior to the deployment of the threads, by manipulating the annular structure.

In some embodiments, the longitudinal wires are configured to position the tubes by adjusting respective circumferential positions of the tubes.

In some embodiments, the longitudinal wires are configured to position the tubes by adjusting respective distances between the tubes and the tissue.

In some embodiments,
the tubes include respective arced distal portions, and
the apparatus further includes a plurality of arced needles disposed within the arced distal portions and coupled to the threads, the arced needles being configured to deploy the threads by arcedly passing, from the arced distal portions, through the tissue.

In some embodiments, the arced distal portions include pointed distal ends, configured to penetrate the tissue prior to the passing of the arced needles through the tissue.

In some embodiments, the arced needles include a plurality of pairs of arced needles, each one of the pairs including a first arced needle, coupled to a first one of the threads, and a second arced needle, coupled to a second one of the threads, and being disposed within a different respective one of the arced distal portions,
the first arced needle and the second arced needle being configured to deploy the first one of the threads and the second one of the threads by arcedly passing through the tissue toward one another.

In some embodiments,
the first arced needle includes a first pointed distal end, to which the first one of the threads is coupled,
the second arced needle includes a second pointed distal end, to which the second one of the threads is coupled, and
the first pointed distal end and the second pointed distal end are configured to couple to one another, following the passing of the first arced needle and the second arced needle through the tissue, such that the first one of the threads is coupled to the second one of the threads.

In some embodiments,
the first arced needle further includes a first needle body reversibly coupled to the first pointed distal end,
the second arced needle further includes a second needle body reversibly coupled to the second pointed distal end, and
the first needle body and the second needle body are configured to detach from, respectively, the first pointed distal end and the second pointed distal end, following the coupling of the first pointed distal end to the second pointed distal end.

In some embodiments, the apparatus further includes:
a hinge, coupled to respective proximal ends of the first arced needle and the second arced needle; and
a hinge-control rod, configured to cause the first arced needle and the second arced needle to pass through the tissue by controlling the hinge.

In some embodiments, the hinge-control rod is configured to cause the first arced needle and the second arced needle to pass through the tissue by opening the hinge.

In some embodiments, each one of the arced needles is disposed within a different respective one of the arced distal portions, and each one of the threads is coupled to a proximal end of a different respective one of the arced needles.

In some embodiments, the apparatus further includes a plurality of shafts coupled to the tubes in contact with the arced needles, the shafts being configured to pass the arced needles through the tissue by rotating.

In some embodiments, the shafts are distal shafts, and the apparatus further includes:
a plurality of proximal shafts; and
a plurality of belts, each one of the belts mechanically coupling at least one of the distal shafts to at least one of the proximal shafts, such that the distal shafts are configured to rotate in response to rotation of the proximal shafts.

There is further provided, in accordance with some embodiments of the present invention, a method that includes expanding an annular assembly of tubes over tissue of a subject, each one of the tubes being slidably disposed within a different respective one of a plurality of flexible tube guides, and carrying a distal end of a different respective one of a plurality of threads. The method further includes, subsequently to expanding the annular assembly of tubes, positioning the tubes, by flexing the tube guides using a plurality of control wires coupled to the tube guides, and, following the positioning of the tubes, passing the threads from the tubes and through the tissue.

In some embodiments, expanding the annular assembly of tubes includes expanding the annular assembly of tubes over an annulus of a valve of a heart of the subject.

In some embodiments,
each one of the control wires includes:
a looped distal end, which is coupled to one of the tube guides,
a first proximal end, and
a second proximal end, and
flexing any one of the tube guides includes flexing the tube guide by moving the first proximal end of the control wire that is coupled to the tube guide with respect to the second proximal end of the control wire that is coupled to the tube guide.

In some embodiments,
the annular structure includes a triangular-wave-shaped ring having alternating top vertices and bottom vertices,
each one of the bottom vertices is coupled to a respective one of the tube guides, and
positioning the tubes includes positioning the tubes by adjusting respective angles of at least some of the top vertices and bottom vertices.

There is further provided, in accordance with some embodiments of the present invention, apparatus for locking an implant over tissue of a subject. The apparatus includes one or more blocks of material, including a proximal face and a distal face, and shaped to define a plurality of lumens that run between the proximal face and the distal face. The apparatus further includes an inner tube, shaped to define a lateral aperture, and being configured to deliver the blocks to the implant while holding the blocks within the inner tube such that a thread passing through the implant loops through the lumens and exits from the inner tube, proximally to the blocks, through the aperture, and while the implant is in contact with the tissue, and an outer tube, configured to cut the thread by sliding over the inner tube and over at least part of the aperture, following the delivery of the blocks to the implant.

In some embodiments, each one of the blocks is disk-shaped.

In some embodiments, the apparatus further includes a rod, configured to facilitate releasing the blocks from the inner tube following the delivery of the blocks to the implant, by pushing the blocks against the implant while the inner tube is withdrawn.

In some embodiments,
the blocks includes a proximal block, which includes the proximal face, and a distal block, which includes the distal face, each of the lumens running through both the proximal block and the distal block,
the inner tube is configured to deliver the blocks to the implant by bringing the distal block into contact with the implant while holding the proximal block at a distance from the distal block, and
the apparatus further includes a rod, configured to push the proximal block onto the distal block, following the delivery of the blocks to the implant.

There is further provided, in accordance with some embodiments of the present invention, a method for locking an implant over tissue of a subject. The method includes looping a thread, which passes through the implant, through one or more blocks of material. The method further includes, subsequently to looping the thread through the blocks, holding the blocks within an inner tube, such that the thread exits from the inner tube, proximally to the blocks, through a lateral aperture of the inner tube. The method further includes, while holding the blocks within the inner tube, delivering the blocks to the implant, while the implant is in contact with the tissue, and, subsequently to delivering the blocks to the implant, cutting the thread, by sliding an outer tube over the inner tube and over at least part of the aperture.

In some embodiments, the tissue includes a valve annulus of the subject.

In some embodiments, looping the thread through the blocks includes looping the thread through the blocks by circling the thread through the blocks between 2 and 10 times.

In some embodiments, the method further includes, while pushing the blocks against the implant, releasing the blocks from the inner tube by withdrawing the inner tube, following the delivery of the blocks to the implant.

The present invention will be more fully understood from the following detailed description of embodiments thereof, taken together with the drawings, in which:

BRIEF DESCRIPTION OF THE DRAWINGS

FIG. 3 is a schematic illustration of a longitudinal cross section through a tube and a tube guide, in accordance with some embodiments of the present invention;

FIG. 4 is a schematic illustration of an alternate thread-deployment apparatus, in accordance with some embodiments of the present invention;

FIGS. 11A-E collectively show the locking of an implant onto tissue, in accordance with some embodiments of the present invention;

FIGS. 12A-D are schematic illustrations showing the positioning of a tube for deployment of a thread therefrom, in accordance with some embodiments of the present invention; and FIGS. 13A-C are schematic illustrations showing the positioning of tubes for deployment of respective threads therefrom, in accordance with some embodiments of the present invention.

DETAILED DESCRIPTION OF EMBODIMENTS

Overview

Figure 1A:
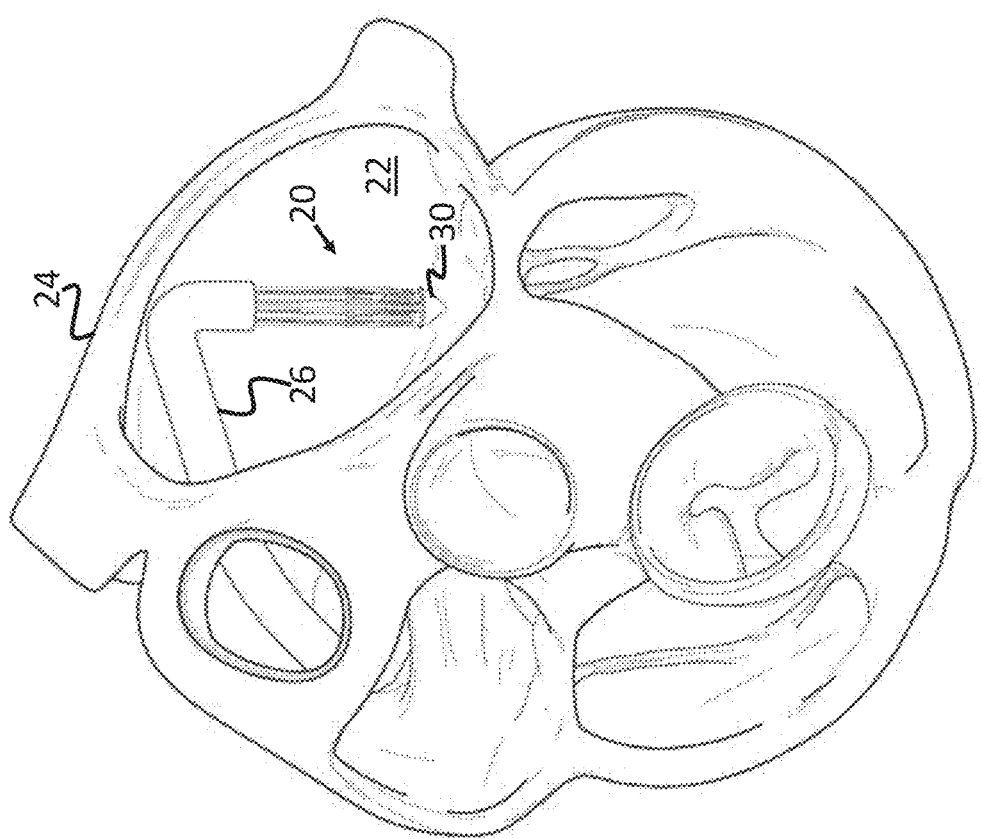
FIGS. 1A-B are schematic illustrations showing the deployment of a thread-deployment apparatus within a left atrium of a heart of a subject, in accordance with some embodiments of the present invention.

Embodiments described herein include apparatus and methods for facilitating the percutaneous implantation of an implant at an implantation site in a subject. For example, embodiments described herein may be used for facilitating the percutaneous implantation of an annuloplasty ring and/or a replacement valve inside the heart, to repair or replace a mitral valve or tricuspid valve.

More specifically, embodiments described herein include a thread-deployment apparatus comprising an annular assembly of tubes, each of which carries the distal end of at least one thread, e.g., by virtue of containing the distal end of the thread. The thread-deployment apparatus further comprises a plurality of flexible tube guides, each of which guides the passage of a respective one of the tubes. An expandable annular structure is coupled, via the tube guides, to the assembly of tubes, and a plurality of looped control wires are coupled to the tube guides.

Prior to the implantation, the annular structure is expanded at the implantation site, thus expanding the tube assembly. The control wires are then used to adjust the positions of the tubes, by flexing the tube guides. Subsequently, the threads are passed, from the tubes, through the tissue at the implantation site, such that each thread extends from the implantation site to the exterior of the subject. The thread-deployment apparatus is then collapsed and withdrawn. Subsequently, the implant is loaded onto the threads, and is then advanced along the threads to the implantation site. Following the placement of the implant at the implantation site, the implant is locked in place, and the threads are then cut.

In some embodiments, the annular structure comprises a triangular-wave-shaped ring having alternating top and bottom vertices, each of the bottom vertices being coupled to a respective one of the tube guides. In such embodiments, the apparatus typically comprises a set of longitudinal wires, which are coupled, respectively, to the top vertices. The longitudinal wires may facilitate the expansion or collapse of the apparatus, and/or may help adjust the positions of the tubes by manipulating the annular structure.

In some embodiments, each tube comprises a pointed distal end, which carries a crimped anchor that is coupled to the distal end of one of the threads. (In such embodiments, each tube, or at least the distal end thereof, may be referred to as a "needle.") For example, the tube may contain the anchor and the distal end of the thread; alternatively, the anchor and the distal end of the thread may be disposed over the distal end of the tube. Subsequently to the tube being positioned as desired by the physician, the pointed distal end of the tube is pushed through the tube guide and through the tissue, until the pointed distal end emerges at the far side of the valve annulus. The anchor is then pushed from the tube (i.e., from within the tube or from the surface of the tube), such that the anchor expands at the distal side of the annulus, thus anchoring the thread in place.

In other embodiments, the threads are looped through the tissue of the annulus, such that it may not be necessary to deploy any anchors to anchor the threads. Typically, in such embodiments, the distal end of each tube is shaped to define a distally-facing crescent that comprises two pointed ends. (Hence, the tube, or at least the distal end thereof, may be referred to as a "double-pointed needle.") The distal end of the tube contains at least one needle that is coupled to a thread. Subsequently to the tube being positioned as desired by the physician, the two pointed ends are pushed into the tissue of the annulus. Subsequently, the needle is passed, from the tube, arcedly through the tissue, thus looping the thread through the tissue.

For example, each tube may contain two arced needles having respective pointed distal ends, which are coupled to different respective threads. In such embodiments, the needles are typically coupled, at their respective proximal ends, to a common hinge, which is controlled by a hinge-control rod passing through the length of the tube to the exterior of the subject. To deploy the threads, the hinge-control rod is used to open the hinge. As the hinge opens, the two needles arcedly pass through the tissue toward one another, until the two distal ends of the needles meet, and become coupled to, one another. Upon the two distal ends becoming coupled to one another, the two threads, which are coupled to the distal ends, effectively become a single thread that loops through the tissue. Subsequently, as the hinge is closed, each distal end becomes uncoupled from the more proximal part of the needle, thus facilitating the withdrawal of the thread-deployment apparatus.

In other embodiments, each tube contains a single arced needle that is coupled to a thread, and one or more circular shafts are in contact with the needle. To deploy the thread, the shafts are rotated, such that the needle—and hence the attached thread—loops through the tissue.

As noted above, subsequently to the deployment of the threads, an implant is passed, over the threads, to the implantation site. Following the placement of the implant at the implantation site, a respective locking element is loaded onto each of the threads, such that the thread loops through the locking element in a manner that inhibits movement of the locking element over the thread in the absence of an applied force of sufficient magnitude. Subsequently, the locking elements are delivered to the implant. Upon coming into contact with the implant, the locking elements lock the implant in place, by virtue of the looping of the threads through the locking elements inhibiting proximal movement of the locking elements. Embodiments of the present invention also include tubes for delivering the locking elements, and for cutting the threads subsequently to the delivery of the locking elements.

Thread-Deployment Apparatus

Figure 1B:
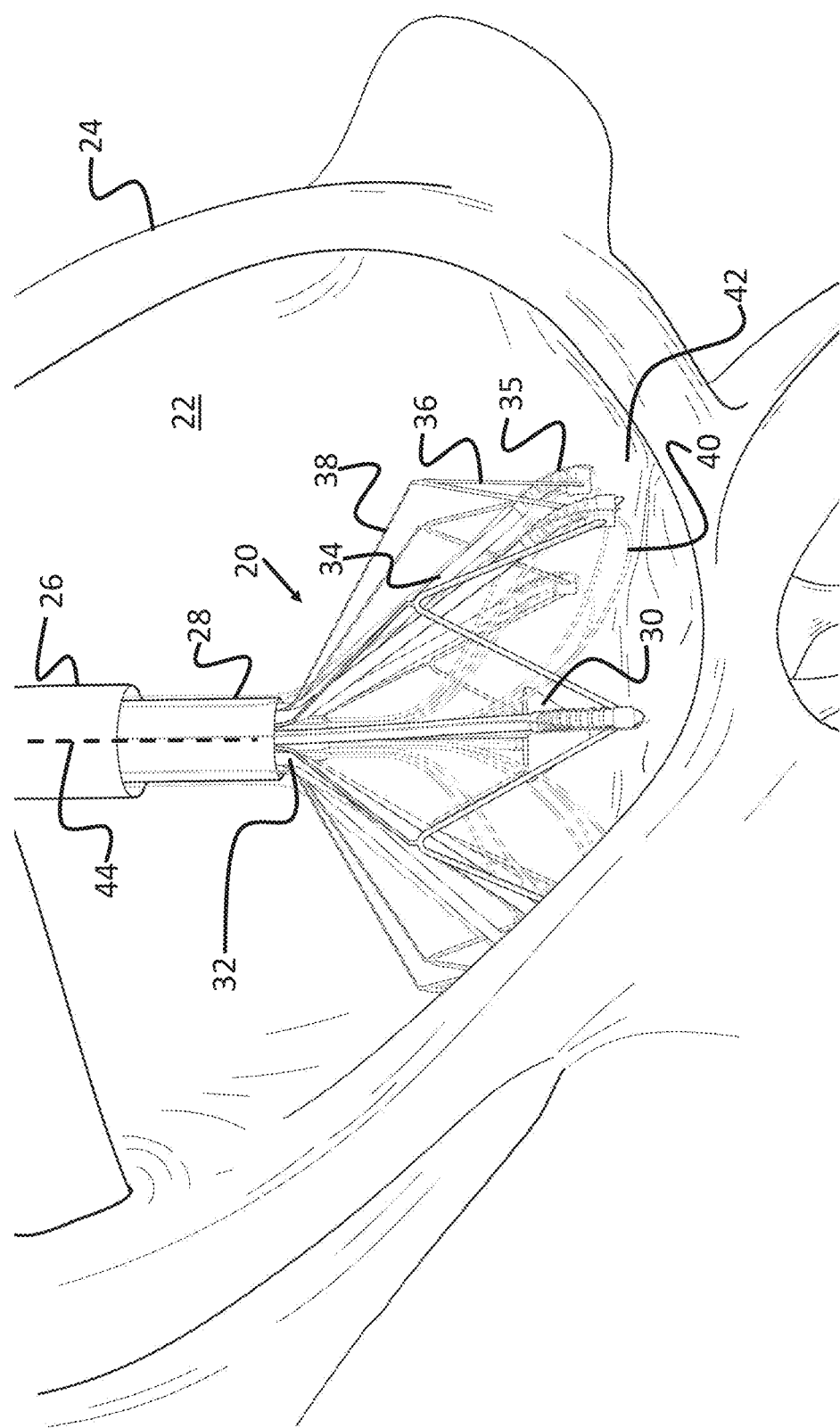

Reference is initially made to FIGS. 1A-B, which are schematic illustrations showing the deployment of a thread-deployment apparatus 20 within a left atrium 22 of a heart 24 of a subject, in accordance with some embodiments of the present invention.

As shown in FIG. 1A, to deliver thread-deployment apparatus 20 to left atrium 22, a sheath 26 is first inserted, percutaneously, into heart 24, e.g., via the femoral vein and inferior vena cava, or via the jugular vein and superior vena cava. Subsequently, techniques known in the art are used to pass sheath 26 through the interatrial septum and into the left atrium. Sheath 26 is typically advanced over a guidewire, under fluoroscopic guidance, and/or under the guidance of any other suitable imaging modality, such as ultrasound (e.g., transthoracic echocardiography (TTE) or transesophageal echocardiography (TEE)), magnetic resonance imaging (MRI), or computed tomography (CT).

Subsequently to delivery of the sheath to the left atrium, apparatus 20 is advanced distally from sheath 26. In some embodiments, as shown in FIG. 1B, a catheter 28 is first advanced from the sheath, and apparatus 20 is then pushed through catheter 28, emerging from the distal end of the catheter.

In some embodiments, as shown in FIGS. 1A-B, sheath 26 is flexed within the left atrium, such that the distal opening of sheath 26 faces the mitral valve. Catheter 28 is similarly flexed. Subsequently, apparatus 20 is pushed, from the distal opening of catheter 28, toward the mitral valve. Alternatively (notwithstanding FIG. 1B), for embodiments in which sheath 26 is flexed within the left atrium, catheter 28 may not be required, and apparatus 20 may be held by, and pushed from, sheath 26.

In other embodiments, sheath 26 is not flexed within the left atrium; rather, catheter 28 is flexed subsequently to being advanced from the sheath, such that the opening of the catheter faces the mitral valve. Apparatus 20 is then advanced from the catheter.

Initially, as shown in FIG. 1A, apparatus 20 is in a collapsed, or "crimped," configuration. In some embodiments, a retaining tip 30, which initially covers the distal end of apparatus 20, holds the apparatus in this collapsed state. Subsequently to the distal advancement of apparatus 20 from sheath 26, retaining tip 30 is pushed off of the distal end of the apparatus, using a pushing wire that passes, from the retaining tip, through the length of sheath 26 to the exterior of the subject. Apparatus 20 may then expand (or "open") within the atrium. Additionally to the removal of retaining tip 30, a slider 32 may be used to open the apparatus, as shown in FIG. 1B and further described below with reference to FIG. 2. Alternatively to using slider 32, a covering sheath may be retracted from over the apparatus.

As shown in FIG. 1B, apparatus 20 comprises an annular assembly (or "collection") of tubes 34, along with a plurality of flexible tube guides 35. Each of tubes 34 is slidably disposed within a respective tube guide 35, such that the tube guide guides the movement of the tube. Typically, each of the tube guides is cylindrical in shape, at least in the absence of any force applied to the tube guide.

Apparatus 20 further comprises an expandable annular structure 36, which is coupled to the tube guides. In some embodiments, annular structure 36 is manufactured from a suitable shape-memory material, e.g., Nitinol. The pushing-off of retaining tip 30, and/or the appropriate movement of slider 32, allows annular structure 36 to expand, such that annular structure 36 expands radially-outward towards its predetermined, "remembered" shape. In other embodiments, annular structure 36 is manufactured from a non-shape-memory material, such as stainless steel, polymeric tubing, and/or any other suitable metals, polymers, or combinations thereof. In such embodiments, the pushing-off of retaining tip 30, and/or the appropriate movement of slider 32, allows annular structure 36 to spring from its crimped configuration. In any case, as the annular structure expands, the annular structure expands the assembly of tubes over the tissue 42 of the subject, by moving tube guides 35 radially outward.

A plurality of threads (not shown) pass from tubes 34 to the exterior of the subject. Following the expansion of the annular structure (and, hence, of the annular assembly of tubes) within the subject, the tubes are positioned and/or oriented over tissue 42, for the subsequent deployment of the threads from the tubes into tissue 42. For example, the tubes may be positioned over the mitral-valve annulus (i.e., at the top face of the annulus, inside the left atrium), for the subsequent deployment of the threads into the annulus.

In general, apparatus 20 may comprise any suitable number of tubes, such as 4-20 tubes. Tubes 34 may be manufactured from any suitable metal or plastic material. Typically, the tubes pass through the entire length of sheath 26, such that, throughout the delivery, deployment, and subsequent use of apparatus 20, the proximal ends of tubes 34 are positioned outside of the subject. Typically, apparatus 20 is rotatable around a central longitudinal axis 44 of the apparatus.

Typically, apparatus 20 comprises a plurality of longitudinal wires 38, which are coupled to the annular structure, typically at the proximal end (or "top") of the annular structure. As further described below with respect to FIG. 2, longitudinal wires 38 may facilitate adjusting the radius of apparatus 20, thus facilitating the positioning of tubes 34 for the deployment of the threads from the tubes, and/or facilitating the crimping of the apparatus following the deployment of the threads. In some embodiments, longitudinal wires 38 may be further used to the manipulate annular structure 36, thus facilitating the positioning of the tubes. For example, by applying a pushing force to the annular structure, longitudinal wires 38 may move annular structure 36 (and hence also the tubes) in the axial direction, i.e., in a direction that is parallel to central longitudinal axis 44, such that each tube is brought into contact with the valve annulus.

In some embodiments, even before the deployment of the threads, at least one tube may pass completely through its tube guide 35, such that the distal end of the tube is distal to the distal end of the tube guide. Typically, however, the distal end of each tube is contained within the corresponding tube guide, and tube is pushed completely through the tube guide only upon the deployment of the thread that is carried by the tube.

Typically, apparatus 20 further comprises a plurality of control wires 40, which are coupled to the respective distal portions of tube guides 35. Control wires 40 are configured to flex the tube guides, thus positioning and/or orienting the tubes for the subsequent deployment of the threads. For example, as further described below with reference to FIGS. 12A-D, to move a thread-deployment position radially inward (i.e., toward axis 44), the relevant tube may be flexed radially inward; conversely, to move the thread-deployment position radially outward, the relevant tube may be flexed radially outward.

Following any necessary positioning and/or orienting of any particular tube 34, the tube penetrates tissue 42, and the thread is then deployed from the tube, i.e., the thread is passed from within the tube, or from the outer surface of the tube, and through the tissue, as further described below with reference to FIG. 3. (The thread may be passed from the outer surface of the tube by retracting the tube, and/or by pushing an anchor, to which the thread is coupled, from the outer surface of the tube.) In some embodiments, all of the threads are deployed after all of the tubes are positioned and/or oriented; alternatively, each thread may be deployed after the tube that carries the thread is positioned and/or oriented, even if some of the other tubes have not yet been positioned and/or oriented.

Although FIGS. 1A-B show the deployment of apparatus 20 specifically within a left atrium, it is noted that apparatus 20 may be similarly deployed at other suitable location within the body of the subject. For example, apparatus 20 may be deployed within the right atrium of the subject, to facilitate the delivery of threads to the tricuspid-valve annulus.

Figure 2:
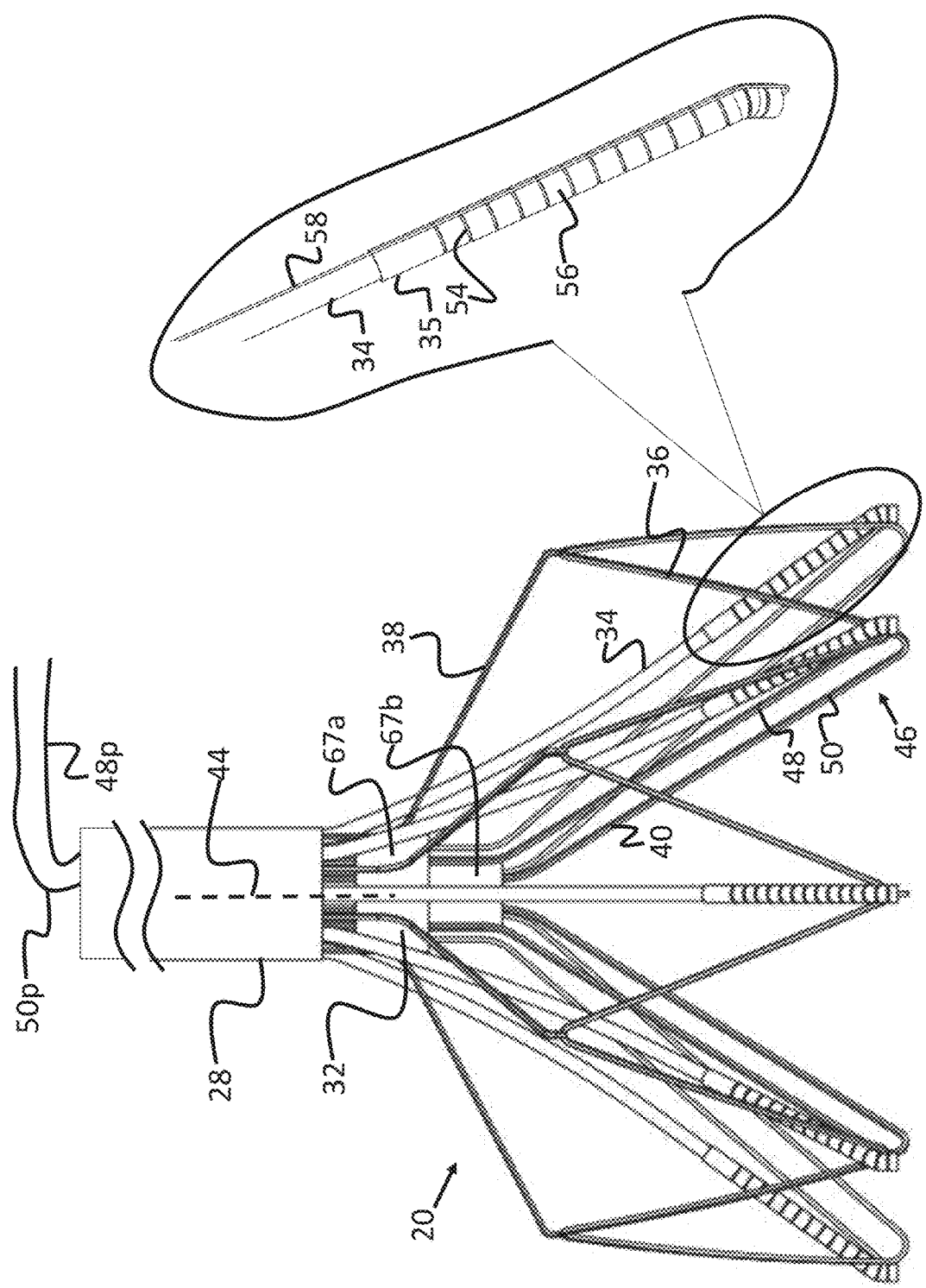
FIG. 2 is a schematic illustration of a thread-deployment apparatus in an expanded configuration, in accordance with some embodiments of the present invention.

Reference is now made to FIG. 2, which is a schematic illustration of thread-deployment apparatus 20 in its expanded configuration, in accordance with some embodiments of the present invention.

Reference is first made to the inset portion of FIG. 2, which shows a tube 34 passing partly through a tube guide 35, along with a thread 58 passing from the distal end of the tube guide.

As described above with reference to FIG. 1B, tube guide 35 is flexible. For example, tube guide 35 may be shaped to define a plurality of circumferential grooves 54. For example, each groove 54 may extend for at least 50%, such as at least 65%, of the circumference of tube guide 35, such that tube guide 35 is divided, by the grooves, into a plurality of semi-connected segments 56. In such embodiments, tube guide 35 is flexible by virtue of grooves 54, in that segments 56 may swivel relative to each other. Alternatively, tube guide 35 may be flexible by virtue of the material from which the tube guide is made, and/or by virtue of any suitable manufacturing process. In general, tube guide 35 may be manufactured from any suitable plastic or metal material, such as Nitinol.

As described above with reference to FIG. 1B, tube guides 35 guide the passage of the tubes, thus facilitating the deployment of threads 58 from the tubes. In some embodiments, prior to threads 58 being deployed, the distal ends of threads 58 are carried inside tubes 34, as further described below with reference to FIG. 3. In such embodiments, threads 58 may pass through the distal ends of tube guides 35, and then run along the outside of tube guides 35 and tubes 34 to the exterior of the subject. Alternatively, instead of passing through the distal ends of the tube guides, threads 58 may pass through apertures in the walls of the tubes, and/or apertures in the walls of the tube guide. As yet another alternative, threads 58 may run inside tubes 34 to the exterior of the subject.

In other embodiments, prior to threads 58 being deployed, the distal ends of threads 58 are carried on the outside surface of tubes 34. For ease of description, however, the remainder of the present description generally assumes that the distal ends of the threads are carried inside tubes 34, as shown in FIG. 2.

Typically, each one of the tube guides is coupled to at least one control wire 40. In some embodiments, as shown in FIG. 2, each of control wires 40 comprises a looped distal end 46, which is coupled to a respective one of the tube guides. Typically, looped distal end 46 is radially-oriented, such that an outer arm 48 of the looped distal end, which is closer to the tube and tube guide, is disposed at a first radius, and an inner arm 50 of the looped distal end, which is further from the tube and tube guide, is disposed at a second radius that is smaller than the first radius. (In this context, the "radius" refers to the distance from axis 44.)

(It is noted that outer arm 48 and inner arm 50 may also be said to belong to the entire control wire, rather than only to looped distal end 46. Thus, for example, it may be said that outer arm 48 and inner arm 50 extend from looped distal end 46 to the exterior of the subject.)

In some embodiments, control wires 40 are directly coupled to the tube guides. In other embodiments, the control wires are indirectly coupled to the tube guides, in that, for example, the control wires are coupled to annular structure 36, which is in turn coupled to the tube guides. It is noted that, in the context of the present application, including the claims, the term "coupled" includes, within it scope, both a direct coupling and an indirect coupling.

Typically, for embodiments in which the control wires are looped, each tube guide is flexed by moving one proximal end of the attached control wire with respect to the other proximal end of the control wire. For example, the proximal end 50p of inner arm 50 may be pulled or pushed, while the proximal end 48p of outer arm 48 is held in place or allowed to freely slide; alternatively, proximal end 48p may be pulled or pushed, while proximal end 50p is held in place or allowed to freely slide. The flexing of the tube guides facilitates positioning the tubes, as further described below with reference to FIGS. 12A-D.

In other embodiments, the control wires are not looped, but rather, are longitudinal, similarly to longitudinal wires 38. Typically, in such embodiments, each tube is coupled to two control wires, with one of the two control wires disposed at a greater radius than the other control wire. (In such embodiments, the outer control wire is analogous to outer arm 48, and hence may be referred to as the "outer control arm," while the inner control wire is analogous to inner arm 50, and hence may be referred to as the "inner control arm.") The two control wires may be coupled to a common point on the tube guide. Alternatively, the outer control wire may be coupled at a slightly more proximal position than the inner control wire. For example, the two control wires may be coupled, respectively, to two different segments 56 belonging to the tube, at a distance of 0.5-10 mm from one another.

In yet other embodiments, a single longitudinal control wire is coupled to each one of the tube guides. In such embodiments, each tube guide may be flexed by moving the attached control wire relative to the tube that passes through the tube guide.

As described above with reference to FIG. 1B, slider 32 may be used to expand (i.e., open) and crimp (i.e., close) both the assembly of tubes 34 and annular structure 36. Typically, slider 32 slides along a "track" that is formed by control wires 40; for example, slider 32 may slide along both inner arms 50 and outer arms 48 of the control wires. When the slider is at (or near) its most distal position on this track, the assembly of tubes, and the annular structure, are held in a crimped position. Hence, to crimp the apparatus, slider 32 may be slid distally along the control wires, such that the slider exerts a crimping force on the tube assembly and the annular structure. Subsequently to the distal sliding of the slider, catheter 28 and/or sheath 26 may be slid distally along longitudinal wires 38, thus further crimping the apparatus. Finally, catheter 28 and/or sheath 26 may be passed over the apparatus. Conversely, to expand the apparatus, slider 32 may be slid proximally along the control wires, such as to allow the annular structure, and hence also the assembly of tubes, to expand.

Typically, each inner arm passes through the slider at a radius that is smaller than the radius at which the corresponding outer arm passes through the slider. For example, slider 32 may comprise a first cylinder 67a, through which the respective outer arms of the control wires pass, and a second cylinder 67b, disposed distally from, and being narrower than (i.e., having a smaller radius than), first cylinder 67a, through which the respective inner arms of the control wires pass. This configuration facilitates the crimping of the apparatus, in that slider 32 may slide to a more distal position than might otherwise be possible.

Typically, annular structure 36 comprises a triangular-wave-shaped ring having alternating top and bottom vertices, each of the bottom vertices being coupled to a respective one of the tube guides. In such embodiments, longitudinal wires 38 are typically coupled to the top vertices of the annular structure. As described above, longitudinal wires 38 facilitate adjusting the radius of apparatus 20, in that the radius may be adjusted by sliding catheter 28 (and/or sheath 26) along the longitudinal wires. This adjustment may facilitate the positioning of tubes 34 for the deployment of the threads from the tubes, and/or the crimping of the apparatus following the deployment of the threads.

Reference is now made to FIG. 3, which is a schematic illustration of a longitudinal cross section through a tube 34 and a tube guide 35, in accordance with some embodiments of the present invention.

In some embodiments, as shown in FIG. 3, each tube 34 comprises a pointed distal end 64. In such embodiments, the distal end of thread 58 is typically disposed near distal end 64, within tube 34. As further shown in FIG. 3, thread 58 may pass through the distal end of the tube and tube guide, and run alongside tube guide 35, and tube 34, to the exterior of the subject. Typically, a plurality of expandable anchors 60 are disposed, respectively, within the tubes, and the distal ends of threads 58 are coupled to the expandable anchors. In such embodiments, a plurality of anchor-pushing elements 62 may be disposed within the tubes, proximally to the anchors.

(For embodiments in which tubes 34 comprise pointed distal ends 64, as in FIG. 3, tubes 34 may alternatively be referred to as "needles," and tube guides 35 as "needle guides." In some embodiments, tube 34 is distally coupled to a needle, comprising distal end 64. In the context of the present application, including the claims, such a needle may be considered to be an extension of the tube.)

To deploy a particular thread, the tube that contains the distal end of the thread is passed through the tissue, such that the thread is also passed through the tissue. (Tubes 34 may extend to the exterior of the subject, in which case the tubes may be pushed directly; alternatively, separate tube-pushing elements, which are disposed proximally to the tubes and extend to the exterior of the subject, may be used to push the tubes.) Subsequently, anchor 60 is pushed from the tube, using anchor-pushing element 62. Upon exiting from the tube, anchor 60 expands at the far side of the tissue (as shown, for example, in FIGS. 11A-E). Subsequently, the tube and anchor-pushing element are retracted into tube guide 35.

Subsequently to the deployment of anchor 60, a pulling force may be continuously applied to thread 58, to hold anchor 60 in place until the implant is locked in place, as described below with reference to FIGS. 11A-E. Alternatively or additionally, a retainer (not shown), coupled to thread 58, may facilitate holding the anchor in place by engaging with the near side of the tissue, as described in International Patent Application Publication WO/2017/187312, whose disclosure is incorporated herein by reference. Such a retainer may, for example, comprise a plurality of prongs, which project radially outward from thread 58.

Figure 6:
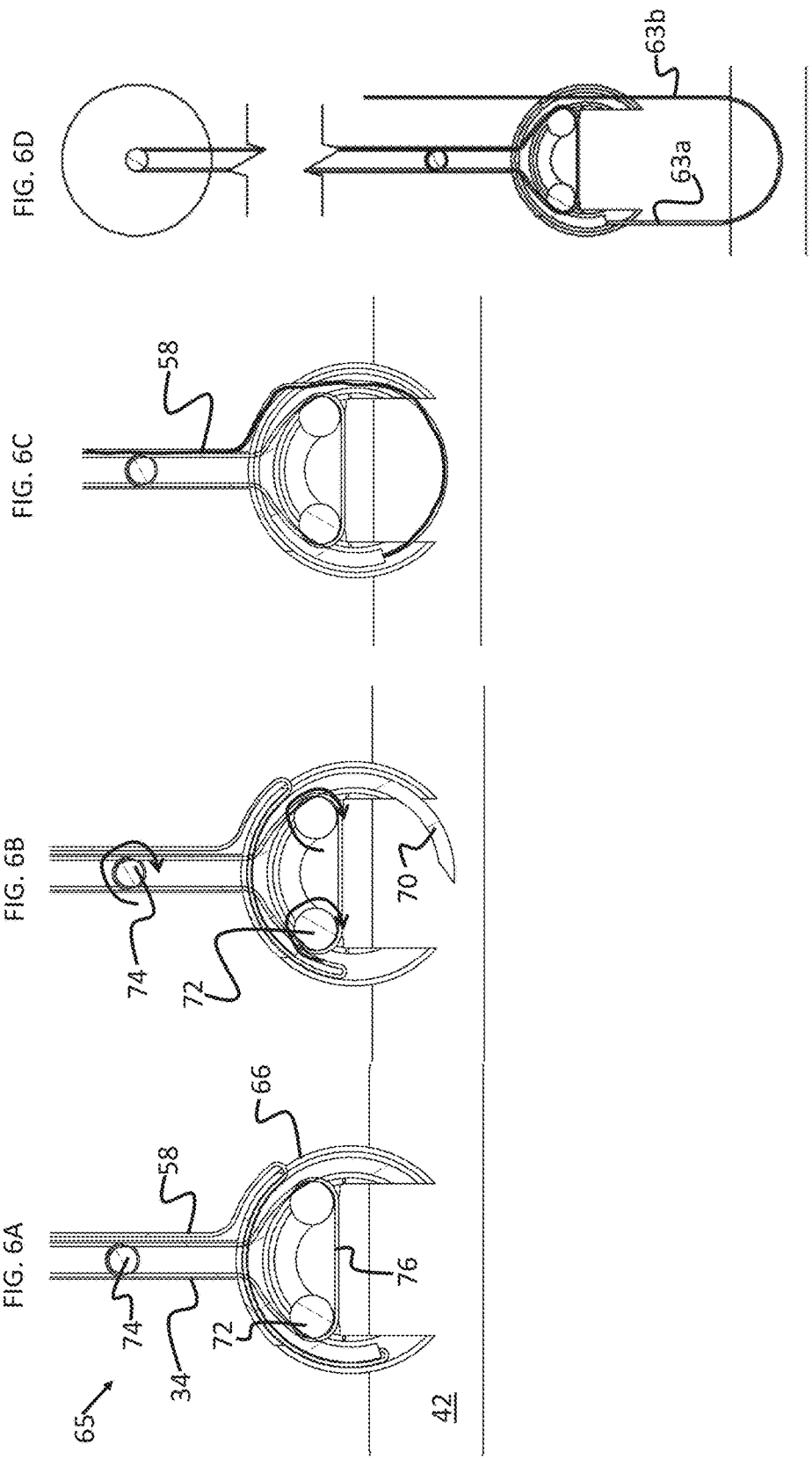
FIGS. 6A-D collectively show the deployment of a thread into tissue by a thread-deploying element, in accordance with some embodiments of the present invention.

As described above with reference to FIG. 1B, tubes 34 may be positioned at the top face of the mitral-valve annulus, within the left atrium. In some embodiments, to deploy anchors 60, tubes 34 are passed through the annulus and into the left ventricle, such that anchors 60 expand within the left ventricle, beneath the leaflets of the valve. In other embodiments, the tubes emerge from the tissue above the leaflets of the valve, within the left atrium. In some embodiments, pointed distal end 64 is curved radially inward, such that the tube exits the valve annulus through the radially-inward-facing face of the valve annulus, as shown, for example, in FIG. 6 of International Patent Application Publication WO/2017/187312, whose disclosure is incorporated herein by reference.

In some embodiments, the tubes penetrate the tissue only after all of the tubes have been appropriately positioned and/or oriented. In other embodiments, at least one of the tubes may penetrate the tissue before all of the tubes have been appropriately positioned and/or oriented, such that the subsequent positioning of the other tubes does not cause the first tube to move from its intended penetration site. For example, the sequence of (i) positioning and/or orienting the tube, (ii) passing the tube through the mitral valve annulus, (iii) passing the tissue anchor from the tube, and (iv) retracting the tube and anchor-pushing element, may be performed one tube at a time, for each of the tubes. Alternatively, for example, after positioning and/or orienting each tube, the tube may penetrate the tissue of the annulus, but the tissue anchors may not be passed from the tube until at least some of the other tubes have also penetrated the tissue.

It is noted that each tube, along with the corresponding tube guide and/or any of the other components described above that facilitate deployment of the thread, may be referred to as a "thread-deploying element," such that apparatus 20 may be referred to as an annular assembly of thread-deploying elements.

Positioning the Tubes

Reference is now made to FIGS. 12A-D, which are schematic illustrations showing the positioning of a tube 34 for deployment of a thread therefrom, in accordance with some embodiments of the present invention.

As described above with reference to FIG. 1B, the control wires may be used to flex tube guides 35 (and hence, to flex the tubes held therein). In general, the flexion of each tube guide may be facilitated by moving the two proximal ends of the control wire that is coupled to the tube guide with respect to one another.

For example, as shown in the left portion of FIG. 12A, tube guide 35 may be flexed radially inward, by pulling proximal end 50p of inner arm 50 while pushing proximal end 48p, holding proximal end 48p in place, or allowing proximal end 48p to freely slide. (Equivalently, to flex the tube guide radially inward, proximal end 48p may be pushed, while pulling proximal end 50p, holding proximal end 50p in place, or allowing proximal end 50p to freely slide.) In other words, by manipulating the control wire as described above, the tube guide may be arced radially inward, such that the tube guide adopts a profile 37, whereby the inner surface of tube guide is concave, and the outer surface of the tube guide is convex.

Conversely, as shown in the left portion of FIG. 12B, tube guide 35 may be flexed radially outward, by pulling proximal end 48p of inner arm 50 while pushing proximal end 50p, holding proximal end 50p in place, or allowing proximal end 50p to freely slide. (Equivalently, to flex the tube guide radially outward, proximal end 50p may be pushed, while pulling proximal end 48p, holding proximal end 48p in place, or allowing proximal end 48p to freely slide.) In other words, by manipulating the control wire as described above, the tube guide may be arced radially outward, such that the tube guide adopts a profile 39, whereby the inner surface of tube guide is convex, and the outer surface of the tube guide is concave.

The right portion of each of FIGS. 12A-B shows an overhead view of a mitral valve 90, with a plurality of tube positions 92 distributed around the inner circumference 94 of the mitral-valve annulus, each such "tube position" being the position of the distal end of a respective tube guide. As shown in these overhead views, by flexing the tube guide as described above (and by virtue of the flexibility of expandable annular structure 36), the distal end of the tube guide may be moved radially inward or outward, i.e., toward or away from inner circumference 94 (and toward or away from central longitudinal axis 44), thus facilitating a better fit of the implant to the valve.

Figure 12C:
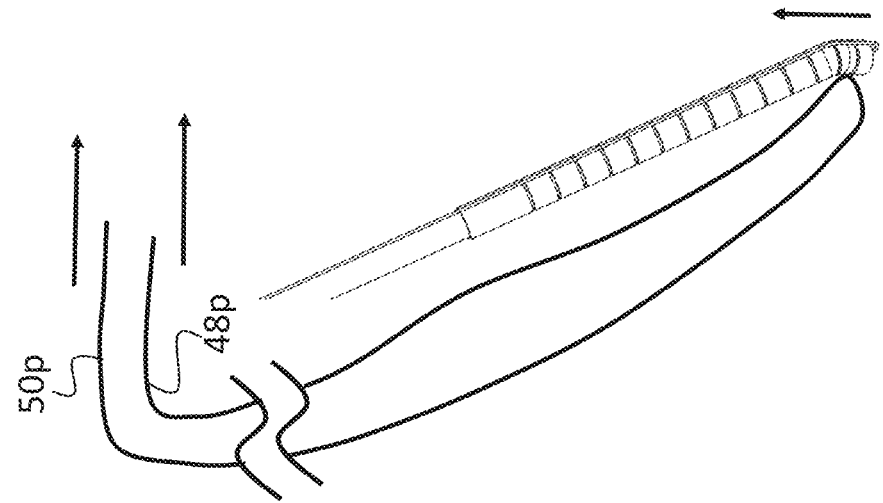
Figure 12D:
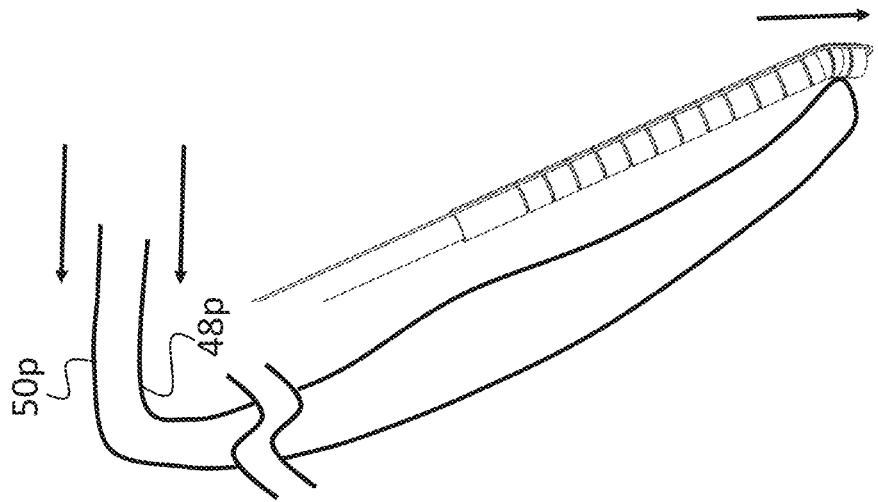

Alternatively or additionally, the control wires may be used to adjust the respective distances of the tubes from the tissue. For example, as shown in FIG. 12C, to move tube 34 distally, toward the tissue, both arms of the control wire may be pushed. Conversely, as shown in FIG. 12D, to move tube 34 proximally, away from the tissue, both arms of the control wire may be pulled.

Typically, the control wires are used primarily for adjusting the radial positions of the tube guides and tubes, and hence, the radial positions at which the threads are deployed through the tissue. For example, to move the tube guide and tube radially inward, tube guide 35 may be first flexed radially inward, as shown in FIG. 12A. Subsequently, the distal end of the tube guide may be pushed back toward the tissue, by pushing both arms of the control wire, as shown in FIG. 12C. (To release the flexion of the tube guide, proximal end 50p may be pushed slightly more than proximal end 48p.) Conversely, to move tube 34 radially outward, the tube guide may be flexed radially outward as shown in FIG. 12B, and then pushed back towards the tissue as shown in FIG. 12C.

Alternatively or additionally to adjusting the radial positions of the tubes, the control wires may be used to adjust the orientations of the tubes—and hence, the angles at which the threads are deployed into the tissue—by flexing the tube guides as described above.

Reference is now made to FIGS. 13A-C, which are schematic illustrations showing the positioning of tubes 34 for deployment of respective threads therefrom, in accordance with some embodiments of the present invention. In general, FIGS. 13A-C complement FIGS. 12A-D, by showing other techniques that may be used to position the tubes, alternatively or additionally to the techniques depicted in FIGS. 12A-D. FIGS. 13A-C depict two neighboring tubes: a first tube 34a, which is slidably disposed within a first tube guide 35a, and a second tube 34b, which is slidably disposed within a second tube guide 35b.

As described above with reference to FIG. 2, annular structure 36 is typically shaped to define a triangular wave; hence, FIGS. 13A-C depict the two neighboring tube guides (and hence, the two neighboring tubes) coupled together by a triangular portion of annular structure 36. In particular, a first arm 96a of the annular structure is coupled to first tube guide 35a, while a second arm 96b of the annular structure is coupled to second tube guide 35b. First arm 96a and second arm 96b meet at a top vertex 98, which is in turn coupled to a wire 38. First arm 96a meets a third arm 96c at a bottom vertex, which is coupled to first tube guide 35a. (The bottom vertex is hidden by the first tube guide.) Similarly, second arm 96b meets a fourth arm (not shown) at another bottom vertex, which is coupled to second tube guide 35b. Typically, both the angles σ of the top vertices (e.g., the angle between first arm 96a and second arm 96b) and the angles θ of the bottom vertices (e.g., the angle between first arm 96a and third arm 96c) are adjustable.

In some embodiments, longitudinal wires 38 are used, in addition to control wires 40, to adjust the positions of the tubes, by manipulating the annular structure. For example, while control wires 40 may be used to adjust the radial positions of the tubes (as described above with reference to FIGS. 12A-D), the longitudinal wires may be used to adjust the respective circumferential positions of the tubes. This adjustment is generally facilitated by the two adjustable angles σ and θ.

For example, as shown in FIG. 13A, by pulling or pushing wire 38, the two neighboring tubes 34a and 34b may be moved, with respect to one another, along the circumference of the tube assembly, i.e., the position 92a of first tube 34a and the position 92b of second tube 34b may be moved, circumferentially, toward or away from one another. In particular, the pulling of wire 38 may decrease angle σ, such that the neighboring tubes are pulled toward one another. (While wire 38 is pulled, control wires 40 may be pushed, such that the pulling of wire 38 does not pull the tubes away from the tissue.) Conversely, the pushing of wire 38 may increase angle σ, such that the neighboring tubes are pushed away from one another.

Alternatively or additionally to adjusting the circumferential positions of the tubes, longitudinal wires 38 may be used to adjust the respective distances of the tubes from tissue 42. (As described above with reference to FIG. 12A-D, this function may alternatively or additionally be performed by control wires 40.) In particular, by pulling wires 38 (without applying a counterforce to control wires 40), the tubes may be pulled away from the tissue; conversely, by pushing wires 38, the tubes may be pushed toward the tissue.

As shown in FIG. 13C, the flexibility of annular structure 36 may further facilitate positioning the tube guides at different "elevations," i.e., the configuration of annular structure 36 may facilitate positioning one of the tube guides more distally than another one of the tube guides. This property facilitates the deployment of the threads through uneven tissue 42.

Alternative Embodiments

Reference is now made to FIG. 4, which is a schematic illustration of an alternate thread-deployment apparatus 20a, in accordance with some embodiments of the present invention.

In general, apparatus 20a is similar to apparatus 20, e.g., with respect to the manner in which expandable annular structure 36 expands the assembly of tubes 34 over the tissue prior to the deployment of the threads, and the manner in which the tubes are positioned and/or oriented. Apparatus 20a differs from apparatus 20, however, with respect to the configuration of tubes 34, and the manner in which the threads are deployed.

In particular, in apparatus 20a, each tube 34 comprises an arced distal portion 66, disposed proximally to tube guide 35. For example, distal portion 66 may be shaped to define a distally-facing crescent, comprising a first tube-end 68a and a second tube-end 68b. In general, arced distal portion 66 is less flexible than more proximal portions of tube 34; for example, arced distal portion 66 may be rigid. (In some embodiments, a portion of tube 34 that is immediately proximal to the arced distal portion may also be rigid.)

As further described below with reference to FIGS. 5 and 7, at least one arced needle is disposed within arced distal portion 66. Each of the arced needles is coupled to the distal end of a respective thread 58 (not shown in FIG. 4), which, as in apparatus 20, may run alongside tube 34, or within tube 34, to the exterior of the subject. As further described below, the arced needles are configured to loop the threads through the tissue of the valve annulus, by arcedly passing, from arced distal portion 66, through the tissue. By virtue of the threads looping through the tissue, it may not be necessary to deploy any anchors.

Typically, first tube-end 68a and second tube-end 68b are pointed. (Thus, as in apparatus 20, tube 34 may be referred to as a "needle," and tube guide 35 may be referred to as a "needle guide.") In such embodiments, to facilitate the deployment of the threads, first tube-end 68a and second tube-end 68b may penetrate the tissue of the annulus, prior to the passing of the arced needle(s) from arced distal portion 66 and through the tissue.

Each tube, along with the arced needle(s) contained therein and/or any of the other components described below that facilitate deployment of the thread(s), may be referred to as a "thread-deploying element," such that apparatus 20a may be referred to as an annular assembly of thread-deploying elements. In this regard, reference is now made to FIG. 5, which is a schematic illustration of a thread-deploying element 65, in accordance with some embodiments of the present invention. (FIG. 5 does not show the portion of tube 34 that is proximal to distal portion 66, or tube guide 35.)

Figure 5:
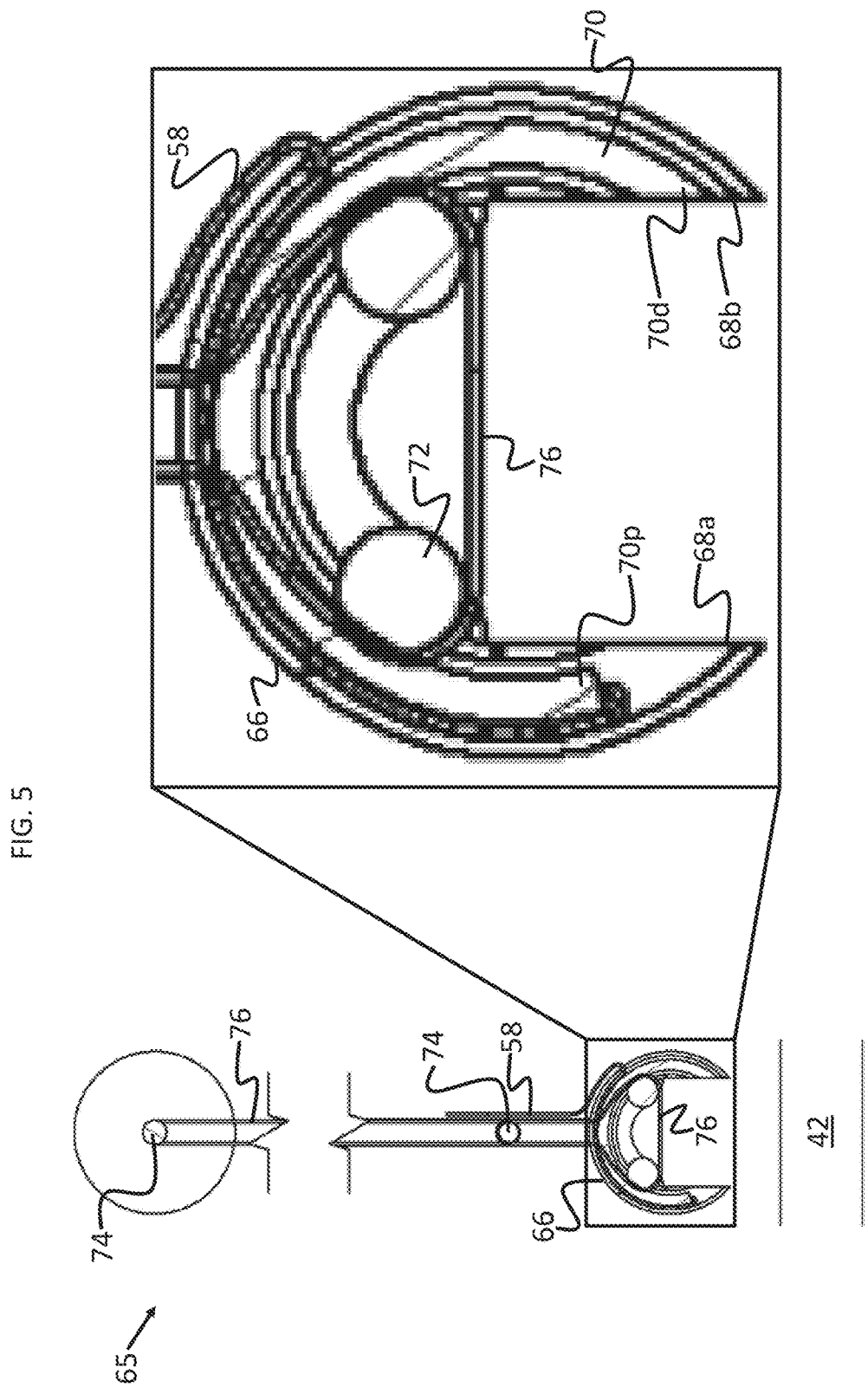
FIG. 5 is a schematic illustration of a thread-deploying element, in accordance with some embodiments of the present invention.

In the particular embodiment shown in FIG. 5, a single arced needle 70, having a pointed distal end 70d, is disposed within arced distal portion 66. Thread 58 is coupled to the proximal end 70p of needle 70. Thread-deploying element 65 comprises one or more (e.g., exactly two) distal shafts 72, which are coupled to the tube in contact with needle 70. As further described below with reference to FIGS. 6A-D, shafts 72 are configured to pass needle 70 through tissue 42, by rotating. Typically, shafts 72 are rotated by rotating one or more proximal shafts 74. For example, one or more belts 76 may, collectively, mechanically couple shafts 72 to each other and to proximal shafts 74, such that distal shafts 72 rotate in response to rotation of the proximal shafts. (It is noted that any shaft that is not in contact with needle 70 is referred to herein as a "proximal shaft," even if the shaft is relatively close to distal portion 66 of the tube.)

Reference is now made to FIGS. 6A-D, which collectively show the deployment of thread 58 into tissue 42 by thread-deploying element 65, in accordance with some embodiments of the present invention.

FIG. 6A shows the penetration of tissue 42 by arced distal portion 66 of tube 34. Following the penetration of the tissue, as shown in FIG. 6B, distal shafts 72 are rotated (via rotation of proximal shafts 74), such that needle 70 arcedly passes, from arced distal portion 66, through tissue 42. (The motion of the needle may also be described as a "rotation.") As the needle passes through the tissue, thread 58, which is coupled to the proximal end of the needle, also passes through the tissue. Typically, the needle is rotated such that the entire needle passes (i) through one of the tube-ends and into the tissue, (ii) through the tissue, and (iii) through the other one of the tube-ends. For example, the needle may undergo a full rotation of 360 degrees.

FIG. 6C shows the configuration of thread-deploying element 65 following the rotation of needle 70. In this configuration, thread 58 arcedly passes through the tissue from one tube-end through the other tube-end, and then, from an aperture in arced distal portion 66, to the exterior of the subject. (For clarity, in FIG. 6C, the path of thread 58 is emphasized.)

As shown in FIG. 6D, following the rotation of the needle, tube 34 is retracted through the tube guide, such that arced distal portion 66 is withdrawn from the tissue. Following the withdrawal of the thread-deploying element, thread 58 loops through tissue 42, such that, following the withdrawal of apparatus 20a from the body of the subject, two different segments of the thread—a first segment 63a and a second segment 63b—pass from the tissue to the exterior of the subject. As further described below with reference to FIG. 9, an implant may be delivered over both of these segments, as if the segments were two separate threads.

Figure 7:
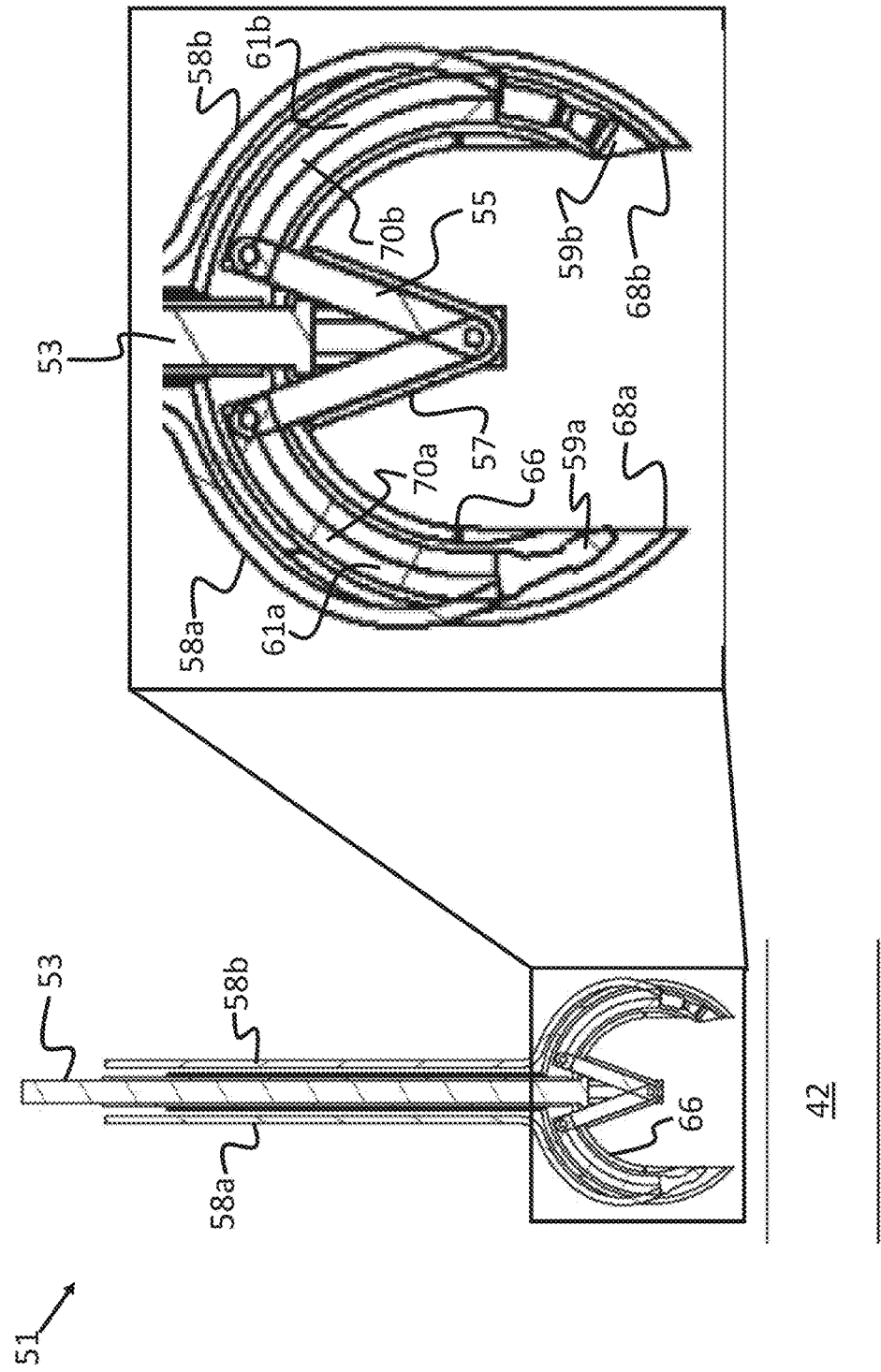
FIG. 7 is a schematic illustration of an alternate thread-deploying element, in accordance with some embodiments of the present invention.

Reference is now made to FIG. 7, which is a schematic illustration of an alternate thread-deploying element 51, in accordance with some embodiments of the present invention. (Similarly to FIG. 5, FIG. 7 does not show the entirety of tube 34, or tube guide 35.)

Thread-deploying element 51 may be used with thread-deployment apparatus 20a (FIG. 4), alternatively or additionally to thread-deploying element 65. Thread-deploying element 51 is similar to thread-deploying element 65 in at least some ways. For example, in thread-deploying element 51, tube 34 comprises arced distal portion 66, comprising tube-ends 68a and 68b. Thread-deploying element 51 also differs from thread-deploying element 65 in at least some ways. For example, instead of a single arced needle, thread-deploying element 51 comprises a pair of arced needles, comprising a first arced needle 70a and a second arced needle 70b. Typically, first arced needle 70a comprises a first pointed distal end 59a and a first needle body 61a, which are reversibly coupled to one another. Similarly, second arced needle 70b comprises a second pointed distal end 59b and a second needle body 61b, which are reversibly coupled to one another. A first thread 58a is coupled to first pointed distal end 59a, while a second thread 58b is coupled to second pointed distal end 59b.

As further described below with reference to FIGS. 8A-D, first arced needle 70a and second arced needle 70b deploy first thread 58a and second thread 58b by arcedly passing through tissue 42, toward one another, from, respectively, first tube-end 68a and second tube-end 68b. Upon the two arced needles colliding with one another within the tissue, first pointed distal end 59a and second pointed distal end 59b couple to one another, such that first thread 58a is coupled to second thread 58b. Thus, the two threads effectively become a single thread that loops through the tissue, similarly to the looping of thread 58 shown in FIG. 6D.

Typically, the respective proximal ends of the arced needles are coupled to a hinge 55, which may be controlled by a hinge-control rod 53. Typically, as shown in FIG. 7, hinge 55 is v-shaped, the respective proximal ends of the arced needles being coupled to the respective ends of the hinge, and the distal end of hinge-control rod 53 being disposed inside of the hinge. A spring (or "clamp") 57 applies a closing force to the hinge, such that, when the distal end of hinge-control rod 53 is at a relatively proximal position (as in FIG. 7), the hinge is almost closed, and the arced needles are inside of arced distal portion 66. Conversely, when hinge-control rod 53 is pushed, against the hinge, to a more distal position, the hinge is opened, causing the arced needles to pass from arced distal portion 66 and through the subject's tissue.

First pointed distal end 59a and second pointed distal end 59b may be configured to couple to one another in any suitable way. For example, as shown in FIG. 7, first pointed distal end 59a may be shaped to define a male connecting tip, and second pointed distal end 59b may be shaped to define a female connecting tip configured to fittingly receive first pointed distal end 59a. Upon a sufficient force being applied to hinge 55 by hinge-control rod 53, first pointed distal end 59a is forced into second pointed distal end 59b.

Reference is now made to FIGS. 8A-D, which collectively show the deployment of threads 58a and 58b into tissue 42 by thread-deploying element 51, in accordance with some embodiments of the present invention.

Figure 8:
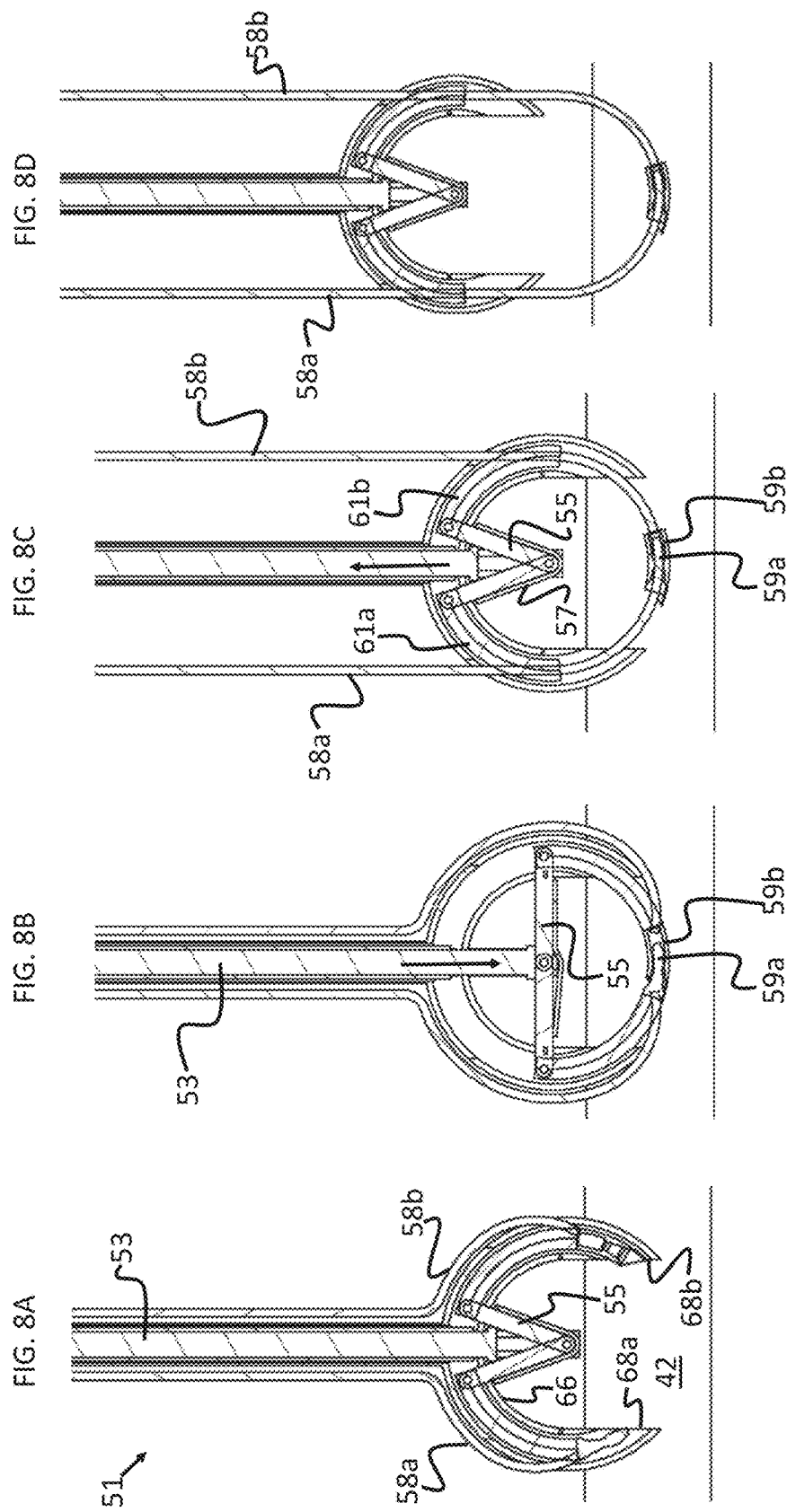
FIGS. 8A-D collectively show the deployment of threads into tissue by a thread-deploying element, in accordance with some embodiments of the present invention.

First, as shown in FIG. 8A, first tube-end 68a and second tube-end 68b penetrate tissue 42. Next, as indicated by the downward-pointing arrow in FIG. 8B, the hinge-control rod is pushed against the hinge, thus causing the hinge to open and passing the arced needles through the tissue. Upon the hinge being sufficiently opened, first pointed distal end 59a couples to second pointed distal end 59b. Subsequently, as indicated by the upward-pointing arrow in FIG. 8C, the hinge-control rod is withdrawn (i.e., moved proximally), such that hinge 55 is closed by spring 57. As the hinge closes, the hinge applies a force to first needle body 61a and second needle body 61b that exceeds the connective force between the needle bodies and the respective distal ends of the needles. Consequently, the needle bodies are detached from the respective distal ends of the needles. Finally, as shown in FIG. 8D, thread-deploying element 51 is withdrawn.

Implant Delivery and Locking

Figure 9:
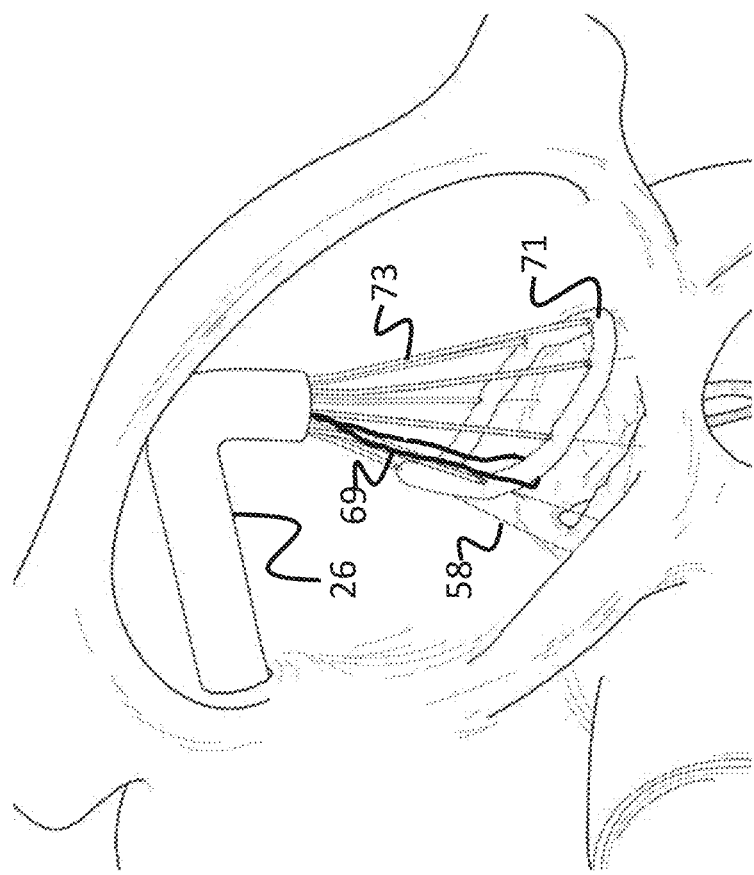
FIG. 9 is a schematic illustration of a delivery of an implant to a mitral-valve annulus, in accordance with some embodiments of the present invention.

Reference is now made to FIG. 9, which is a schematic illustration of a delivery of an implant 71 to a mitral-valve annulus, in accordance with some embodiments of the present invention.

Following the deployment of threads 58, apparatus 20 or apparatus 20a is crimped, inserted into catheter 28 and/or sheath 26, and then withdrawn from the subject. Subsequently, an implant 71, such as an annuloplasty ring or replacement valve, may be delivered to the mitral valve annulus over the threads.

First, implant 71 is loaded onto the threads, by passing the proximal ends of the threads through respective apertures in the implant. (It is noted the implant may be loaded onto the threads even before the threads are deployed.) A single thread that loops through the tissue, as described above for apparatus 20a, may function as two separate threads, in that each segment (or "arm") of the loop may pass through a different respective aperture in the implant.

Next, a plurality of hollow pushing rods 73 may be loaded onto the threads, proximally to the implant. Pushing rods 73 may then push the implant through sheath 26, along the threads, to the valve annulus. It is noted that pushing rods 73, along with any other rods described herein, are typically flexible, such that the rods may follow any number of turns within the body of the subject.

In some embodiments, one or more retraction-threads 69 are looped around implant 71. If the physician ascertains that the implant was improperly positioned (i.e., that the threads were improperly placed), decides to replace implant 71 with another implant (e.g., due to implant 71 being improperly sized or shaped), or decides not to perform any implantation at all, retraction-threads 69 may be used to retract implant 71. Subsequently, if no implantation is to be performed, there is no need to operate invasively on the subject; rather, provided that anchors 60 are held in place by the aforementioned retainers, it may be sufficient to simply cut threads 58.

Figure 10:
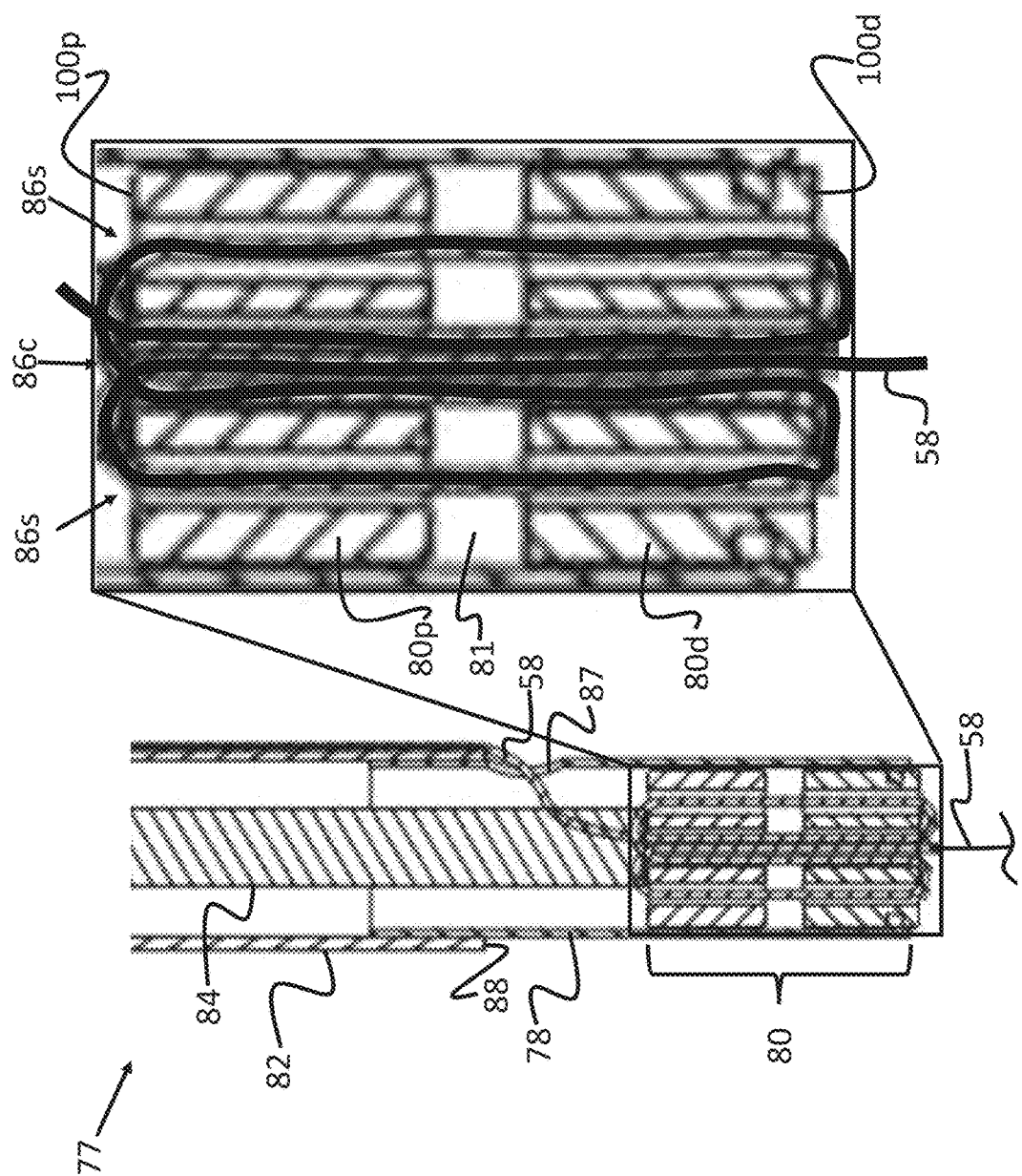
FIG. 10 is a schematic illustration of a locking apparatus for locking an implant over the valve annulus of a subject, in accordance with some embodiments of the present invention.

Reference is now made to FIG. 10, which is a schematic illustration of a locking apparatus 77 for locking implant 71 over the valve annulus of the subject, in accordance with some embodiments of the present invention.

Subsequently to the delivery of the implant to the valve annulus as shown in FIG. 9, pushing rods 73 are withdrawn, and a plurality of locking apparatuses 77 are then loaded onto the threads. (Typically, one locking apparatus is loaded onto each of the threads.) Locking apparatus 77 comprises an inner tube 78, and one or more blocks of material (e.g., any biocompatible, rigid plastic or metal material), which are referred to herein, collectively, as a locking element 80. Locking element 80 comprises a proximal face 100*p* and a distal face 100*d*, and is shaped to define a plurality of lumens that run between proximal face 100*p* and distal face 100*d*. Each locking apparatus is loaded onto its corresponding thread by looping the thread through the lumens of the locking element. As further described below with reference to FIGS. 11A-E, inner tube 78 is configured to hold locking element 80 within the inner tube, and to deliver the locking element to the implant over thread 58 while the implant is in contact with the tissue of the subject. Subsequently to the delivery of locking element 80, thread 58 is cut proximally to the locking element, and inner tube 78 is withdrawn.

By virtue of thread 58 looping through the lumens of the locking element, a frictional force is generated as the locking element slides along the thread. This frictional force inhibits the locking element from sliding proximally along the thread, following the delivery of the locking element to the implant. Hence, the locking element, when in contact with the implant at the implantation site, locks the implant in place, by inhibiting the implant from migrating from the implantation site.

In general, the locking element may be shaped to define any suitable number of lumens. FIG. 10 shows one possible embodiment, in which locking element 80 is shaped to define three lumens: a central lumen 86*c*, and two side lumens 86*s*. Thread 58 may loop through the locking element (i.e., through the lumens of the locking element) in any suitable manner Typically, the thread is looped through the locking element such that the thread circles through the locking element between 1 and 10 times, e.g., between 2 and 10 times. For example, given the three lumens shown in FIG. 10, thread 58 may be looped through the locking element such that thread 58 circles twice through the locking element before passing to the proximal end of the locking element. In particular, the thread may pass, from the distal end of locking element 80, proximally through central lumen 86*c*, distally through one of side lumens 86*s*, proximally through the central lumen, distally through the other one of the side lumens, and then proximally through the central lumen.

In some embodiments, locking element 80 comprises a proximal block of material 80*p*, which comprises proximal face 100*p*, and a distal block of material 80*d*, which comprises distal face 100*d*. In such embodiments, each of the lumens runs through both proximal block 80*p* and distal block 80*d*. (Equivalently, it may be said that each of the proximal block and distal block is shaped to define a plurality of lumens, the lumens of the proximal block being aligned with those of the distal block.) When delivering the locking element to the implant, proximal block 80*p* is held by inner tube 78 proximally to, and at a distance from, distal block 80*d*, with a gap 81 separating between the distal and proximal blocks. Gap 81 facilitates the delivery of the locking element to the implant, by reducing the friction that is generated as the locking element passes over the thread. As further described below with reference to FIG. 11B, subsequently to the delivery of the locking element to the implant, a rod 84, disposed within inner tube 78, pushes the proximal block onto the distal block. The pushing of the proximal block onto the distal block increases the frictional force between the locking element and the thread, such that the locking element is unlikely to move proximally along the thread.

In other embodiments, locking element 80 comprises a single block of material that, alone, generates sufficient friction to inhibit movement of the locking element along the thread in the absence of a sufficient applied force. In such embodiments, the locking element may be delivered to the implant by pulling the thread taut, and applying a pushing force to inner tube 78 that is sufficient to overcome the friction generated between the thread and the locking element.

In general, locking element 80 may have any suitable shape. For example, each of proximal block 80*p* and distal block 80*d* may be disk-shaped, or the locking element may comprise a single, disk-shaped block of material. Typically, the thickness of the locking element—i.e., the distance between proximal face 100*p* and distal face 100*d*—is between 2 and 6 mm. For example, in embodiments in which the locking element comprises two blocks of material, the thickness of each block—i.e., the distance between the proximal face and the distal face of each block—may be between 1 and 3 mm.

Typically, inner tube 78 is shaped to define a lateral aperture 87 in the wall of the tube. Thread 58 is passed through aperture 87, such that the thread exits from the inner tube, proximally to locking element 80, through aperture 87. As further described below with reference to FIG. 11C, subsequently to the delivery of locking element 80 to the implant, as the thread is pulled taut, an outer tube 82, which is slidably disposed over inner tube 78, is slid distally over the inner tube. As outer tube 82 passes over aperture 87, a sharp distal edge 88 of the outer tube cuts thread 58. (Equivalently, to cut the thread, the inner tube may be withdrawn while the outer tube is held in place. In the context of the present application, including the claims, such a maneuver is also said to comprise a sliding of the outer tube over the inner tube.)

In some embodiments, locking apparatuses 77 are also used to deliver the implant, in place of pushing rods 73. That is, locking elements 80 are loaded onto the threads proximally to the implant, and locking apparatuses 77 then push implant 71 to the valve annulus.

Reference is now made to FIGS. 11A-E, which collectively show the locking of implant 71 onto tissue 42, in accordance with some embodiments of the present invention.

Each of FIGS. 11A-E shows a transverse cross-section through implant 71, with thread 58 passing from anchor 60, through tissue 42, and through the implant. By virtue of showing anchor 60, FIGS. 11A-E assume that thread-deployment apparatus 20 was used to deploy thread 58. It is noted, however, that the techniques described herein with reference to FIG. 11A-E may also be practiced in a scenario in which the thread loops through the tissue, following the deployment of the thread by alternate thread-deployment apparatus 20*a*.

FIG. 11A shows the configuration of locking apparatus 77, following the delivery of locking element 80, over thread 58, to implant 71. In particular, in this configuration, inner tube 78 holds the locking element (e.g., by squeezing, i.e., exerting a radially-inward force on, the locking element), with distal block 80*d* in contact with the implant, and with proximal block 80*p* being at a small distance from distal block 80*d*.

As indicated by the downward-pointing arrow in FIG. 11B, subsequently to the delivery of the locking element, rod 84 pushes the proximal block onto the distal block. Next, as indicated by the downward-pointing arrow in FIG. 11C, outer tube 82 is pushed, such that the outer tube slides over the inner tube and over at least part of aperture 87. As outer tube 82 passes over aperture 87, outer tube 82 cuts the thread, i.e., the outer tube severs the distal portion of the thread, which loops through the locking element and passes through the implant, from the more proximal portion of the thread. In some embodiments, outer tube 82 continues to be pushed after the thread is cut, until the outer tube reaches the distal end of the inner tube. Following the cutting of the thread, the more proximal portion of the thread may be removed from the subject.

Subsequently to the cutting of the thread, as indicated by the upward-pointing arrow in FIG. 11D, the inner tube is withdrawn, i.e., pulled proximally, while rod 84 pushes the locking element against the implant, such that the inner tube slides from over the locking element. The inner tube, outer tube, and rod are then withdrawn from the subject. Subsequently, as shown in FIG. 11E, the locking element continues to hold implant 71 in place, by virtue of the looping of thread 58 through the locking element.

As noted above with reference to FIG. 10, in some embodiments, locking element 80 comprises a single block, rather than separate proximal and distal blocks. Even in such embodiments, however, locking apparatus 77 typically comprises rod 84, since, as described immediately above, rod 84 facilitates releasing the locking element from the inner tube, by pushing the locking element against the implant such that the locking element is not pulled away from the implant as the inner tube is withdrawn.

It is noted that, notwithstanding the particular applications described herein, locking apparatus 77 may be used to lock any suitable implant over any type of tissue.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. For example, slider 32 (FIG. 2) may be used, independently from one or more of the related components of apparatus 20 described above, to open or close any suitable expandable apparatus. As another example, tubes 34 comprising arced distal portions 66 (FIG. 4) may be used, independently from one or more of the related components of apparatus 20a described above, for any suitable thread-deploying application.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus, comprising:
 a plurality of flexible tube guides;
 an annular assembly of tubes, each of the tubes being slidably disposed within a respective one of the tube guides;
 a plurality of threads, each of which comprising a distal end that is carried by a respective one of the tubes;
 an expandable annular structure coupled to the tube guides, configured to expand the assembly of tubes, from a collapsed configuration, over tissue of a subject, by moving the tube guides radially outward; and
 a plurality of control wires coupled to the tube guides, configured to position the tubes, subsequently to the expansion of the assembly, for deployment of the threads from the tubes and into the tissue, by flexing the tube guides.

2. The apparatus according to claim 1, wherein the distal end of each one of the threads is disposed within the respective one of the tubes.

3. The apparatus according to claim 1, wherein each one of the tube guides is coupled to at least one of the control wires.

4. The apparatus according to claim 3, wherein each one of the tube guides is coupled to two of the control wires.

5. The apparatus according to claim 3, wherein each one of the control wires comprises a looped distal end, and wherein each one of the tube guides is coupled to the looped distal end of a respective one of the control wires.

6. The apparatus according to claim 5, wherein the looped distal end comprises:
 an outer arm, to which the tube guide is coupled, disposed at a first radius; and
 an inner arm, disposed at a second radius that is smaller than the first radius.

7. The apparatus according to claim 1,
 wherein the tubes comprise respective pointed distal ends configured to pass through the tissue prior to the deployment of the threads, and
 wherein the apparatus further comprises:
 a plurality of expandable anchors disposed, respectively, within the tubes, and coupled to the respective distal ends of the threads; and
 a plurality of anchor-pushing elements disposed, respectively, within the tubes proximally to the anchors, the anchor-pushing elements being configured to deploy the threads by pushing the anchors from the tubes, subsequently to the pointed distal ends of the tubes passing through the tissue.

8. The apparatus according to claim 1, further comprising a slider,
 wherein the control wires pass through the slider, and
 wherein the slider is configured to expand the assembly of tubes by sliding proximally along the control wires.

9. The apparatus according to claim 8, wherein each one of the control wires comprises:
 a looped distal end;
 an outer arm, which extends proximally from the looped distal end, and which passes through the slider at a first radius; and
 an inner arm, which extends proximally from the looped distal end, and which passes through the slider at a second radius that is smaller than the first radius.

10. The apparatus according to claim 1,
 wherein the annular structure comprises a triangular-wave-shaped ring having alternating top vertices and bottom vertices, and
 wherein each one of the bottom vertices is coupled to a respective one of the tube guides.

11. The apparatus according to claim 10, wherein respective angles of the top vertices and bottom vertices are adjustable.

12. The apparatus according to claim 1, further comprising a plurality of longitudinal wires coupled to the annular structure, configured to facilitate crimping the annular structure following the deployment of the threads.

13. The apparatus according to claim 12, wherein the longitudinal wires are further configured to position the tubes prior to the deployment of the threads, by adjusting respective circumferential positions of the tubes.

14. The apparatus according to claim 12, wherein the longitudinal wires are further configured to position the tubes prior to the deployment of the threads, by adjusting respective distances between the tubes and the tissue.

15. The apparatus according to claim 1,
wherein the tubes comprise respective arced distal portions, and
wherein the apparatus further comprises a plurality of arced needles disposed within the arced distal portions and coupled to the threads, the arced needles being configured to deploy the threads by arcedly passing, from the arced distal portions, through the tissue.

16. The apparatus according to claim 15, wherein the arced distal portions comprise pointed distal ends, configured to penetrate the tissue prior to the passing of the arced needles through the tissue.

17. The apparatus according to claim 15, wherein the arced needles comprise a plurality of pairs of arced needles, each one of the pairs comprising a first arced needle, coupled to a first one of the threads, and a second arced needle, coupled to a second one of the threads, and being disposed within a different respective one of the arced distal portions, the first arced needle and the second arced needle being configured to deploy the first one of the threads and the second one of the threads by arcedly passing through the tissue toward one another.

18. The apparatus according to claim 17,
wherein the first arced needle comprises a first pointed distal end, to which the first one of the threads is coupled,
wherein the second arced needle comprises a second pointed distal end, to which the second one of the threads is coupled, and
wherein the first pointed distal end and the second pointed distal end are configured to couple to one another, following the passing of the first arced needle and the second arced needle through the tissue, such that the first one of the threads is coupled to the second one of the threads.

19. The apparatus according to claim 18,
wherein the first arced needle further comprises a first needle body reversibly coupled to the first pointed distal end,
wherein the second arced needle further comprises a second needle body reversibly coupled to the second pointed distal end, and
wherein the first needle body and the second needle body are configured to detach from, respectively, the first pointed distal end and the second pointed distal end, following the coupling of the first pointed distal end to the second pointed distal end.

20. The apparatus according to claim 17, further comprising:
a hinge, coupled to respective proximal ends of the first arced needle and the second arced needle; and
a hinge-control rod, configured to cause the first arced needle and the second arced needle to pass through the tissue by controlling the hinge.

21. The apparatus according to claim 20, wherein the hinge-control rod is configured to cause the first arced needle and the second arced needle to pass through the tissue by opening the hinge.

22. The apparatus according to claim 15, wherein each one of the arced needles is disposed within a different respective one of the arced distal portions, and wherein each one of the threads is coupled to a proximal end of a different respective one of the arced needles.

23. The apparatus according to claim 22, further comprising a plurality of shafts coupled to the tubes in contact with the arced needles, the shafts being configured to pass the arced needles through the tissue by rotating.

24. The apparatus according to claim 23, wherein the shafts are distal shafts, and wherein the apparatus further comprises:
a plurality of proximal shafts; and
a plurality of belts, each one of the belts mechanically coupling at least one of the distal shafts to at least one of the proximal shafts, such that the distal shafts are configured to rotate in response to rotation of the proximal shafts.

25. A method, comprising:
expanding an annular assembly of tubes over tissue of a subject, each one of the tubes being slidably disposed within a different respective one of a plurality of flexible tube guides, and carrying a distal end of a different respective one of a plurality of threads;
subsequently to expanding the annular assembly of tubes, positioning the tubes, by flexing the tube guides using a plurality of control wires coupled to the tube guides; and
following the positioning of the tubes, passing the threads from the tubes and through the tissue.

26. The method according to claim 25,
wherein each one of the control wires includes:
a looped distal end, which is coupled to one of the tube guides,
a first proximal end, and
a second proximal end, and
wherein flexing any one of the tube guides comprises flexing the tube guide by moving the first proximal end of the control wire that is coupled to the tube guide with respect to the second proximal end of the control wire that is coupled to the tube guide.

27. The method according to claim 25,
wherein expanding the assembly of tubes comprises expanding the assembly of tubes by allowing an expandable annular structure, which includes a triangular-wave-shaped ring having alternating top vertices and bottom vertices and is coupled to the tube guides, to expand,
wherein each one of the bottom vertices is coupled to a respective one of the tube guides, and
wherein positioning the tubes comprises positioning the tubes by adjusting respective angles of at least some of the top vertices and bottom vertices.

28. The method according to claim 25, wherein the tubes include respective arced distal portions, and wherein passing the threads from the tubes comprises passing the threads from the tubes by arcedly passing a plurality of arced needles, which are coupled, respectively, to the threads, from the arced distal portions of the tubes.

29. The method according to claim 28,
wherein the arced needles include a plurality of pairs of arced needles, each one of the pairs including a first arced needle, coupled to a first one of the threads, and a second arced needle, coupled to a second one of the threads, and being disposed within a different respective one of the arced distal portions, and
wherein deploying the threads comprises deploying the threads by arcedly passing each one of the pairs of arced needles through the tissue, toward one another.

30. The method according to claim 28, wherein each one of the arced needles is disposed within a different respective one of the arced distal portions, and wherein each one of the threads is coupled to a proximal end of a different respective one of the arced needles.

* * * * *